(12) United States Patent
Yu et al.

(10) Patent No.: US 11,123,400 B2
(45) Date of Patent: Sep. 21, 2021

(54) BROKEN OR FOLDED HELICAL PEPTIDE OR PEPTIDE ANALOG EXHIBITING ANTIMICROBIAL ACTIVITY AGAINST GRAM-NEGATIVE BACTERIA, AND USE THEREOF

(71) Applicant: SEOUL NATIONAL UNIVERSITY R&DB FOUNDATION, Seoul (KR)

(72) Inventors: Jaehoon Yu, Gyeonggi-do (KR); Yan Lee, Seoul (KR); Soonsil Hyun, Seoul (KR); Seo Yeon Kim, Seoul (KR); Sun Mi Jin, Seoul (KR); Yunhwa Choi, Seoul (KR); Doyeon Jo, Seoul (KR); Seonju Lee, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 15/761,089

(22) PCT Filed: Sep. 19, 2016

(86) PCT No.: PCT/KR2016/010408
§ 371 (c)(1),
(2) Date: Mar. 17, 2018

(87) PCT Pub. No.: WO2017/048092
PCT Pub. Date: Mar. 23, 2017

(65) Prior Publication Data
US 2018/0339016 A1    Nov. 29, 2018

(30) Foreign Application Priority Data

Sep. 17, 2015 (KR) .......... 10-2015-0131555
Sep. 19, 2016 (KR) .......... 10-2016-0119524

(51) Int. Cl.
| | | |
|---|---|---|
| A61K 38/10 | (2006.01) |
| A01N 37/18 | (2006.01) |
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| A61K 38/16 | (2006.01) |
| C07K 7/08 | (2006.01) |
| A61K 31/616 | (2006.01) |
| A61K 31/431 | (2006.01) |
| A61K 31/192 | (2006.01) |
| A61K 31/05 | (2006.01) |
| A61K 31/12 | (2006.01) |
| A61K 31/5377 | (2006.01) |
| A61K 31/366 | (2006.01) |
| A61P 31/04 | (2006.01) |
| A61P 29/00 | (2006.01) |
| A61P 9/00 | (2006.01) |
| A61K 38/06 | (2006.01) |
| A61K 38/00 | (2006.01) |
| A61K 47/64 | (2017.01) |

(52) U.S. Cl.
CPC .............. *A61K 38/16* (2013.01); *A61K 31/05* (2013.01); *A61K 31/12* (2013.01); *A61K 31/192* (2013.01); *A61K 31/366* (2013.01); *A61K 31/431* (2013.01); *A61K 31/5377* (2013.01); *A61K 31/616* (2013.01); *A61K 38/04* (2013.01); *A61K 38/06* (2013.01); *A61K 38/10* (2013.01); *A61P 9/00* (2018.01); *A61P 29/00* (2018.01); *A61P 31/04* (2018.01); *C07K 7/08* (2013.01); *A61K 38/00* (2013.01); *A61K 47/6455* (2017.08)

(58) Field of Classification Search
None
See application file for complete search history.

(56) References Cited

U.S. PATENT DOCUMENTS

| | | | | |
|---|---|---|---|---|
| 6,140,306 | A * | 10/2000 | Lambert, Jr. ........... | A61P 31/04 514/2.2 |
| 2006/0057668 | A1 * | 3/2006 | Yoshida .................... | A61P 1/02 435/69.1 |
| 2007/0042492 | A1 | 2/2007 | Avrameas | |

(Continued)

FOREIGN PATENT DOCUMENTS

| | | |
|---|---|---|
| CN | 1735422 A | 2/2006 |
| CN | 101991593 A | 3/2011 |

(Continued)

OTHER PUBLICATIONS

Hwang et al., ChemMedChem 8:59-62 (2013) (Year: 2013).*
Wampler, "The 20 Amino Acids and Their Role in Protein Structures" available online at http://www.proteinstructures.com/Structure/Structure/amino-acids.html, 3 pages (2010) (Year: 2010).*
"Amphipathic" available online at http://www.biology-online.org/dictionary/Amphipathic, 1 page (2010) (Year: 2010).*
Zelezetsky et al., Biochim. Biophys. Acta 1758:1436-1449 (2006) (Year: 2006).*

(Continued)

*Primary Examiner* — Thea D' Ambrosio
(74) *Attorney, Agent, or Firm* — Hultquist, PLLC; Steven J. Hultquist

(57) ABSTRACT

The present invention relates to a broken or kinked helical peptide or peptide analogue and the use thereof, and more particularly to a Gram-negative bacterial membrane-penetrating peptide or peptide analogue wherein an alpha-helical amphipathic peptide composed of hydrophobic amino acids and hydrophilic amino acids has a kinked structure, or an antimicrobial composition employing the specific activity of the peptide against the Gram-negative bacterial membrane, or an antimicrobial composition for co-administration, or a conjugate comprising a drug linked to the peptide or peptide analogue, or an antibiotic comprising the same.

3 Claims, 10 Drawing Sheets
(9 of 10 Drawing Sheet(s) Filed in Color)
Specification includes a Sequence Listing.

(56) References Cited

U.S. PATENT DOCUMENTS

| | | | |
|---|---|---|---|
| 2008/0096245 A1 | | 4/2008 | Decarolis et al. |
| 2016/0229894 A1* | | 8/2016 | Yu .......................... C07K 7/08 |

FOREIGN PATENT DOCUMENTS

| | | | |
|---|---|---|---|
| JP | S5264432 A | 5/1977 | |
| JP | 2002501079 A | 1/2002 | |
| JP | 2002519385 A | 7/2002 | |
| JP | 2002528120 A | 9/2002 | |
| JP | 2007-502262 A | 2/2007 | |
| JP | 2008536495 A | 9/2008 | |
| JP | 2010504919 A | 2/2010 | |
| JP | 2010507576 A | 3/2010 | |
| JP | 2012508806 A | 4/2012 | |
| KR | 1020030061718 A | 7/2003 | |
| KR | 20100010338 A | 2/2010 | |
| KR | 20150012505 A | 2/2015 | |
| WO | 2007013487 A1 | 2/2007 | |
| WO | WO2015057009 A1 | 4/2015 | |
| WO | WO2016085280 A1 | 6/2016 | |

OTHER PUBLICATIONS

Merriam-Webster, "Microbe", available online at https://www.merriam-webster.com/dictionary/microbe, 17 pages (accessed on Oct. 23, 2019) (Year: 2019).*

Anygen Co. machine translation of Korean Publication No. 2003-0061718 published on Jul. 22, 2003 (Year: 2003).*

Loho et al., Acta Med. Indones.-Indones. J. Intern. Med. 47:157-168 (Apr. 2015) (Year: 2015).*

"The 20 Amino Acids and Their Role in Protein Structure", available online at https://proteinstructures.com/Structure/Structure/amino-acids.html, 4 pages (first available 2010) (Year: 2010).*

AnaSpec, "Temporin L, amide," available online at https://www.anaspec.com/products/product.asp?id=53269#:~:text=Peptides%20%3E%20Temporins%20%3E%3E%20Temporin%20L%2C%20amide&text=This%20peptide%20is%20active%20against,%2Dnegative%20bacteria%2C%20including%20B, 1 page (accessed on Jul. 30, 2020) (Year: 2020).*

Washington et al., Mayo Clin Proc 60:189-203 (1985) (Year: 1985).*

Tyagi et al., PLoS ONE 10:e0121313, 15 pages (Mar. 2015) (Year: 2015).*

Park et al., Peptide Sci. 96:130-136 (2010) (Year: 2010).*

"Chloramphenicol," available online at http://www.antimicrobe.org/drugpopup/Chloramphenicol.pdf, 2 pages (first available Sep. 6, 2015) (Year: 2015).*

Son et al., ChemMedChem 8:1638-1642 (2013) (Year: 2013).*

"Amikacin (Injection Route)," available online at https://www.mayoclinic.org/drugs-supplements/amikacin-injection-route/description/drg-20074493, 7 pages (last updated 2021) (Year: 2021).*

Sharma et al., Front. Biol. 9:287-290 (2014) (Year: 2014).*

Bommineni, Y., et al., "Fowlicidin-3 is an alpha-helical Cationic Host Defense Peptide With Potent Antibacterial and Lipopolysaccharide-neutralizing Activities", "FEBS Journal", 2007, pp. 418-428, vol. 274.

Jang, S.A., et al., "Mechanism of Action and Specificity of Antimicrobial Peptides Designed Based on Buforin IIb", "Peptides", 2012, pp. 283-289, vol. 34.

Kim, S., et al., "Nonhemolytic Cell-Penetrating Peptides: Site Specific Introduction of Glutamine and Lysine Residues Into the alpha-Helical Peptide Causes Deletion of Its Direct Membrane Disrupting Ability but Retention of Its Cell Penetrating Ability", "Biomacromolecules", 2016, pp. 3007-3015, vol. 17.

Lee, J.K., et al., "A Proline-Hinge Alters the Characteristics of the Amphipathic alpha-helical AMPs", "PLOS One", 2013, pp. e67597 1-9, vol. 8, No. 7.

Meng, H., et al., "Antimicrobial Activity and Protease Stability of Peptides Containing Fluorinated Amino Acids", "J. Am. Chem. Soc.", 2007, pp. 15615-15622, vol. 129.

He, J., et al., "A lack of synergy between membrane-permeabilizing cationic antimicrobial peptides and conventional antibodies", "Biochimica et Biophysica Acta", 2014, pp. 1-8, Publisher: www.elsevier.com/locate/bbamem.

He, J., "Design and Study of Novel Antimicrobial Peptides with Proline Substitution", "Dissertation presented to Faculty of The College of Arts and Sciences of Ohio University", Nov. 2009, pp. 1-228.

He, J., et al., "A Lack of Synergy Between Membrane-Permeabilizing Cationic Antimicrobial Peptides and Conventional Antibiotics", "Biochimica et Biophysica Acta", 2015, pp. 8-15, vol. 1848.

Avitabile, C., et al., "Design, Structural and Functional Characterization of a Temporin-1b Analog Active Against Gram-Negative Bacteria", "Biochimica et Biophysica Acta", 2013, pp. 3767-3775, vol. 1830.

\* cited by examiner

KL-L9P            LK-L12P

SEQUENCE LISTING

<160> NUMBER OF SEQ ID NOS: 75

<210> SEQ ID NO 1
<211> LENGTH: 5
<212> TYPE: PRT
<213> ORGANISM: Artificial Sequence
<220> FEATURE:
<223> OTHER INFORMATION: peptide

<400> SEQUENCE: 1

Lys Leu Leu Lys Leu
1               5

<210> SEQ ID NO 2
<211> LENGTH: 5
<212> TYPE: PRT
<213> ORGANISM: Artificial Sequence
<220> FEATURE:
<223> OTHER INFORMATION: peptide

<400> SEQUENCE: 2

Leu Lys Lys Leu Leu
1               5

<210> SEQ ID NO 3
<211> LENGTH: 7
<212> TYPE: PRT
<213> ORGANISM: Artificial Sequence
<220> FEATURE:
<223> OTHER INFORMATION: peptide

<400> SEQUENCE: 3

Leu Lys Lys Leu Leu Lys Leu
1               5

<210> SEQ ID NO 4
<211> LENGTH: 7
<212> TYPE: PRT
<213> ORGANISM: Artificial Sequence
<220> FEATURE:
<223> OTHER INFORMATION: peptide

<400> SEQUENCE: 4

Lys Leu Leu Lys Leu Leu Lys
1               5

<210> SEQ ID NO 5
<211> LENGTH: 14
<212> TYPE: PRT
<213> ORGANISM: Artificial Sequence
<220> FEATURE:
<223> OTHER INFORMATION: peptide

<400> SEQUENCE: 5

Leu Lys Lys Leu Leu Lys Leu Leu Lys Lys Leu Leu Lys Leu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: peptide

<400> SEQUENCE: 6

Lys Leu Leu Lys Leu Leu Lys Lys Leu Leu Lys Leu Leu Lys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: LK-L4P

<400> SEQUENCE: 7

Leu Lys Lys Pro Leu Lys Leu Leu Lys Lys Leu Leu Lys Leu
1               5                   10

<210> SEQ ID NO 8
<211> LENGTH: 14
<212> TYPE: PRT
<213> ORGANISM: Artificial Sequence
<220> FEATURE:
<223> OTHER INFORMATION: LK-L5P

<400> SEQUENCE: 8

Leu Lys Lys Leu Pro Lys Leu Leu Lys Lys Leu Leu Lys Leu
1               5                   10

<210> SEQ ID NO 9
<211> LENGTH: 14
<212> TYPE: PRT
<213> ORGANISM: Artificial Sequence
<220> FEATURE:
<223> OTHER INFORMATION: LK-K6P

<400> SEQUENCE: 9

Leu Lys Lys Leu Leu Pro Leu Leu Lys Lys Leu Leu Lys Leu
1               5                   10

<210> SEQ ID NO 10
<211> LENGTH: 14
<212> TYPE: PRT
<213> ORGANISM: Artificial Sequence
<220> FEATURE:
<223> OTHER INFORMATION: LK-L7P

<400> SEQUENCE: 10

Leu Lys Lys Leu Leu Lys Pro Leu Lys Lys Leu Leu Lys Leu
1               5                   10

<210> SEQ ID NO 11
<211> LENGTH: 14
<212> TYPE: PRT
<213> ORGANISM: Artificial Sequence
<220> FEATURE:
<223> OTHER INFORMATION: LK-L8P

<400> SEQUENCE: 11

Leu Lys Lys Leu Leu Lys Leu Pro Lys Lys Leu Leu Lys Leu
1               5                   10

<210> SEQ ID NO 12
<211> LENGTH: 14
<212> TYPE: PRT
<213> ORGANISM: Artificial Sequence
<220> FEATURE:
<223> OTHER INFORMATION: LK-K9P

<400> SEQUENCE: 12

Leu Lys Lys Leu Leu Lys Leu Leu Pro Lys Leu Leu Lys Leu
1               5                   10

```
<210> SEQ ID NO 13
<211> LENGTH: 14
<212> TYPE: PRT
<213> ORGANISM: Artificial Sequence
<220> FEATURE:
<223> OTHER INFORMATION: LK-K10P

<400> SEQUENCE: 13

Leu Lys Lys Leu Leu Lys Leu Leu Lys Pro Leu Leu Lys Leu
1               5                   10

<210> SEQ ID NO 14
<211> LENGTH: 14
<212> TYPE: PRT
<213> ORGANISM: Artificial Sequence
<220> FEATURE:
<223> OTHER INFORMATION: LK-L11P

<400> SEQUENCE: 14

Leu Lys Lys Leu Leu Lys Leu Leu Lys Lys Pro Leu Lys Leu
1               5                   10

<210> SEQ ID NO 15
<211> LENGTH: 14
<212> TYPE: PRT
<213> ORGANISM: Artificial Sequence
<220> FEATURE:
<223> OTHER INFORMATION: LK-L12P

<400> SEQUENCE: 15

Leu Lys Lys Leu Leu Lys Leu Leu Lys Lys Leu Pro Lys Leu
1               5                   10

<210> SEQ ID NO 16
<211> LENGTH: 14
<212> TYPE: PRT
<213> ORGANISM: Artificial Sequence
<220> FEATURE:
<223> OTHER INFORMATION: KL-L2P

<400> SEQUENCE: 16

Lys Pro Leu Lys Leu Leu Lys Lys Leu Leu Lys Leu Leu Lys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: KL-L3P

<400> SEQUENCE: 17

Lys Leu Pro Lys Leu Leu Lys Lys Leu Leu Lys Leu Leu Lys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: KL-L5P

<400> SEQUENCE: 18

Lys Leu Leu Lys Pro Leu Lys Lys Leu Leu Lys Leu Leu Lys
1               5                   10
```

```
<210> SEQ ID NO 19
<211> LENGTH: 14
<212> TYPE: PRT
<213> ORGANISM: Artificial Sequence
<220> FEATURE:
<223> OTHER INFORMATION: KL-L6P

<400> SEQUENCE: 19

Lys Leu Leu Lys Leu Pro Lys Lys Leu Lys Leu Leu Lys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: KL-K7P

<400> SEQUENCE: 20

Lys Leu Leu Lys Leu Leu Pro Lys Leu Lys Leu Leu Lys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: KL-K8P

<400> SEQUENCE: 21

Lys Leu Leu Lys Leu Leu Lys Pro Leu Lys Leu Leu Lys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: KL-L9P

<400> SEQUENCE: 22

Lys Leu Leu Lys Leu Leu Lys Lys Pro Leu Leu Leu Lys
1               5                   10

<210> SEQ ID NO 23
<211> LENGTH: 14
<212> TYPE: PRT
<213> ORGANISM: Artificial Sequence
<220> FEATURE:
<223> OTHER INFORMATION: KL-L10P

<400> SEQUENCE: 23

Lys Leu Leu Lys Leu Leu Lys Lys Leu Pro Leu Leu Lys
1               5                   10

<210> SEQ ID NO 24
<211> LENGTH: 14
<212> TYPE: PRT
<213> ORGANISM: Artificial Sequence
<220> FEATURE:
<223> OTHER INFORMATION: KL-L12P

<400> SEQUENCE: 24

Lys Leu Leu Lys Leu Leu Lys Lys Leu Leu Lys Pro Leu Lys
1               5                   10

<210> SEQ ID NO 25
```

```
<211> LENGTH: 14
<212> TYPE: PRT
<213> ORGANISM: Artificial Sequence
<220> FEATURE:
<223> OTHER INFORMATION: KL-L13P

<400> SEQUENCE: 25

Lys Leu Leu Lys Leu Leu Lys Lys Leu Lys Leu Leu Pro Lys
1               5                   10

<210> SEQ ID NO 26
<211> LENGTH: 14
<212> TYPE: PRT
<213> ORGANISM: Artificial Sequence
<220> FEATURE:
<223> OTHER INFORMATION: KL L9G

<400> SEQUENCE: 26

Lys Leu Leu Lys Leu Leu Lys Lys Gly Leu Lys Leu Leu Lys
1               5                   10

<210> SEQ ID NO 27
<211> LENGTH: 14
<212> TYPE: PRT
<213> ORGANISM: Artificial Sequence
<220> FEATURE:
<223> OTHER INFORMATION: KL L9S

<400> SEQUENCE: 27

Lys Leu Leu Lys Leu Leu Lys Lys Ser Leu Lys Leu Leu Lys
1               5                   10

<210> SEQ ID NO 28
<211> LENGTH: 14
<212> TYPE: PRT
<213> ORGANISM: Artificial Sequence
<220> FEATURE:
<223> OTHER INFORMATION: KL L9N

<400> SEQUENCE: 28

Lys Leu Leu Lys Leu Leu Lys Lys Asn Leu Lys Leu Leu Lys
1               5                   10

<210> SEQ ID NO 29
<211> LENGTH: 14
<212> TYPE: PRT
<213> ORGANISM: Artificial Sequence
<220> FEATURE:
<223> OTHER INFORMATION: KL L9Q

<400> SEQUENCE: 29

Lys Leu Leu Lys Leu Leu Lys Lys Gln Leu Lys Leu Leu Lys
1               5                   10

<210> SEQ ID NO 30
<211> LENGTH: 14
<212> TYPE: PRT
<213> ORGANISM: Artificial Sequence
<220> FEATURE:
<223> OTHER INFORMATION: KL L9D

<400> SEQUENCE: 30

Lys Leu Leu Lys Leu Leu Lys Lys Asp Leu Lys Leu Leu Lys
1               5                   10

<210> SEQ ID NO 31
<211> LENGTH: 14
```

```
<212> TYPE: PRT
<213> ORGANISM: Artificial Sequence
<220> FEATURE:
<223> OTHER INFORMATION: KL L9E

<400> SEQUENCE: 31

Lys Leu Leu Lys Leu Leu Lys Lys Glu Leu Lys Leu Leu Lys
1               5                   10

<210> SEQ ID NO 32
<211> LENGTH: 14
<212> TYPE: PRT
<213> ORGANISM: Artificial Sequence
<220> FEATURE:
<223> OTHER INFORMATION: KL-L9P/K1A

<400> SEQUENCE: 32

Ala Leu Leu Lys Leu Leu Lys Lys Pro Leu Lys Leu Leu Lys
1               5                   10

<210> SEQ ID NO 33
<211> LENGTH: 14
<212> TYPE: PRT
<213> ORGANISM: Artificial Sequence
<220> FEATURE:
<223> OTHER INFORMATION: KL-L9P/K4A

<400> SEQUENCE: 33

Lys Leu Leu Ala Leu Leu Lys Lys Pro Leu Lys Leu Leu Lys
1               5                   10

<210> SEQ ID NO 34
<211> LENGTH: 14
<212> TYPE: PRT
<213> ORGANISM: Artificial Sequence
<220> FEATURE:
<223> OTHER INFORMATION: KL-L9P/K7A

<400> SEQUENCE: 34

Lys Leu Leu Lys Leu Leu Ala Lys Pro Leu Lys Leu Leu Lys
1               5                   10

<210> SEQ ID NO 35
<211> LENGTH: 14
<212> TYPE: PRT
<213> ORGANISM: Artificial Sequence
<220> FEATURE:
<223> OTHER INFORMATION: KL-L9P/K8A

<400> SEQUENCE: 35

Lys Leu Leu Lys Leu Leu Lys Ala Pro Leu Lys Leu Leu Lys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: KL-L9P/K11A

<400> SEQUENCE: 36

Lys Leu Leu Lys Leu Leu Lys Lys Pro Leu Ala Leu Leu Lys
1               5                   10

<210> SEQ ID NO 37
<211> LENGTH: 14
<212> TYPE: PRT
```

-continued

<213> ORGANISM: Artificial Sequence
<220> FEATURE:
<223> OTHER INFORMATION: KL-L9P/K14A

<400> SEQUENCE: 37

Lys Leu Leu Lys Leu Leu Lys Lys Pro Leu Lys Leu Leu Ala
1               5                   10

<210> SEQ ID NO 38
<211> LENGTH: 14
<212> TYPE: PRT
<213> ORGANISM: Artificial Sequence
<220> FEATURE:
<223> OTHER INFORMATION: 7,10 kink KL-L9P

<400> SEQUENCE: 38

Lys Leu Leu Lys Leu Leu Cys Lys Leu Cys Lys Leu Leu Lys
1               5                   10

<210> SEQ ID NO 39
<211> LENGTH: 14
<212> TYPE: PRT
<213> ORGANISM: Artificial Sequence
<220> FEATURE:
<223> OTHER INFORMATION: 8,12 kink KL-L9P

<400> SEQUENCE: 39

Lys Leu Leu Lys Leu Leu Lys Cys Leu Leu Lys Cys Leu Lys
1               5                   10

<210> SEQ ID NO 40
<211> LENGTH: 25
<212> TYPE: PRT
<213> ORGANISM: Artificial Sequence
<220> FEATURE:
<223> OTHER INFORMATION: st 3,11 KL-L9P

<400> SEQUENCE: 40

Lys Leu Arg Arg Arg Arg Arg Arg Arg Lys Leu Leu Lys Lys Pro
1               5                   10                  15

Leu Ser Ser Ser Ser Ser Leu Leu Lys
            20                  25

<210> SEQ ID NO 41
<211> LENGTH: 14
<212> TYPE: PRT
<213> ORGANISM: Artificial Sequence
<220> FEATURE:
<223> OTHER INFORMATION: LK-L4PL5P

<400> SEQUENCE: 41

Leu Lys Lys Pro Pro Lys Leu Leu Lys Lys Leu Leu Lys Leu
1               5                   10

<210> SEQ ID NO 42
<211> LENGTH: 14
<212> TYPE: PRT
<213> ORGANISM: Artificial Sequence
<220> FEATURE:
<223> OTHER INFORMATION: LK-L4PL8P

<400> SEQUENCE: 42

Leu Lys Lys Pro Leu Lys Leu Pro Lys Lys Leu Leu Lys Leu
1               5                   10

<210> SEQ ID NO 43

<211> LENGTH: 14
<212> TYPE: PRT
<213> ORGANISM: Artificial Sequence
<220> FEATURE:
<223> OTHER INFORMATION: LK-L4PL11P

<400> SEQUENCE: 43

Leu Lys Lys Pro Leu Lys Leu Lys Lys Pro Leu Lys Leu
1               5                   10

<210> SEQ ID NO 44
<211> LENGTH: 14
<212> TYPE: PRT
<213> ORGANISM: Artificial Sequence
<220> FEATURE:
<223> OTHER INFORMATION: LK-L5PL8P

<400> SEQUENCE: 44

Leu Lys Lys Leu Pro Lys Leu Pro Lys Leu Leu Lys Leu
1               5                   10

<210> SEQ ID NO 45
<211> LENGTH: 14
<212> TYPE: PRT
<213> ORGANISM: Artificial Sequence
<220> FEATURE:
<223> OTHER INFORMATION: LK-L5PL11P

<400> SEQUENCE: 45

Leu Lys Lys Leu Pro Lys Leu Leu Lys Pro Leu Lys Leu
1               5                   10

<210> SEQ ID NO 46
<211> LENGTH: 14
<212> TYPE: PRT
<213> ORGANISM: Artificial Sequence
<220> FEATURE:
<223> OTHER INFORMATION: LK-L7P8P

<400> SEQUENCE: 46

Leu Lys Lys Leu Leu Lys Pro Pro Lys Leu Leu Lys Leu
1               5                   10

<210> SEQ ID NO 47
<211> LENGTH: 14
<212> TYPE: PRT
<213> ORGANISM: Artificial Sequence
<220> FEATURE:
<223> OTHER INFORMATION: LK-L7PL11P

<400> SEQUENCE: 47

Leu Lys Lys Leu Leu Lys Pro Leu Lys Pro Leu Lys Leu
1               5                   10

<210> SEQ ID NO 48
<211> LENGTH: 14
<212> TYPE: PRT
<213> ORGANISM: Artificial Sequence
<220> FEATURE:
<223> OTHER INFORMATION: LK-L8PL11P

<400> SEQUENCE: 48

Leu Lys Lys Leu Leu Lys Leu Pro Lys Pro Leu Lys Leu
1               5                   10

<210> SEQ ID NO 49
<211> LENGTH: 14

```
<212> TYPE: PRT
<213> ORGANISM: Artificial Sequence
<220> FEATURE:
<223> OTHER INFORMATION: LK-L11PL12P

<400> SEQUENCE: 49

Leu Lys Lys Leu Leu Lys Leu Leu Lys Lys Pro Pro Lys Leu
1               5                   10

<210> SEQ ID NO 50
<211> LENGTH: 21
<212> TYPE: PRT
<213> ORGANISM: Artificial Sequence
<220> FEATURE:
<223> OTHER INFORMATION: buforin

<400> SEQUENCE: 50

Thr Arg Ser Ser Arg Ala Gly Leu Gln Phe Pro Val Gly Arg Val His
1               5                   10                  15

Arg Leu Leu Arg Lys
            20

<210> SEQ ID NO 51
<211> LENGTH: 17
<212> TYPE: PRT
<213> ORGANISM: Artificial Sequence
<220> FEATURE:
<223> OTHER INFORMATION: buforin 5-20

<400> SEQUENCE: 51

Arg Ala Gly Leu Gln Phe Pro Val Gly Arg Val His Arg Leu Leu Arg
1               5                   10                  15

Lys

<210> SEQ ID NO 52
<211> LENGTH: 14
<212> TYPE: PRT
<213> ORGANISM: Artificial Sequence
<220> FEATURE:
<223> OTHER INFORMATION: KL-L2AL9P

<400> SEQUENCE: 52

Lys Ala Leu Lys Leu Leu Lys Lys Pro Leu Lys Leu Leu Lys
1               5                   10

<210> SEQ ID NO 53
<211> LENGTH: 14
<212> TYPE: PRT
<213> ORGANISM: Artificial Sequence
<220> FEATURE:
<223> OTHER INFORMATION: KL-L3AL9P

<400> SEQUENCE: 53

Lys Leu Ala Lys Leu Leu Lys Lys Pro Leu Lys Leu Leu Lys
1               5                   10

<210> SEQ ID NO 54
<211> LENGTH: 14
<212> TYPE: PRT
<213> ORGANISM: Artificial Sequence
<220> FEATURE:
<223> OTHER INFORMATION: LK-L5AL9P

<400> SEQUENCE: 54

Lys Leu Leu Lys Ala Leu Lys Lys Pro Leu Lys Leu Leu Lys
1               5                   10
```

<210> SEQ ID NO 55
<211> LENGTH: 14
<212> TYPE: PRT
<213> ORGANISM: Artificial Sequence
<220> FEATURE:
<223> OTHER INFORMATION: KL-L6AL9P

<400> SEQUENCE: 55

Lys Leu Leu Lys Leu Ala Lys Lys Pro Leu Lys Leu Leu Lys
1               5                   10

<210> SEQ ID NO 56
<211> LENGTH: 14
<212> TYPE: PRT
<213> ORGANISM: Artificial Sequence
<220> FEATURE:
<223> OTHER INFORMATION: KL-L9PL10A

<400> SEQUENCE: 56

Lys Leu Leu Lys Leu Leu Lys Lys Pro Ala Lys Leu Leu Lys
1               5                   10

<210> SEQ ID NO 57
<211> LENGTH: 14
<212> TYPE: PRT
<213> ORGANISM: Artificial Sequence
<220> FEATURE:
<223> OTHER INFORMATION: KL-L9PL12A

<400> SEQUENCE: 57

Lys Leu Leu Lys Leu Leu Lys Lys Pro Leu Lys Ala Leu Lys
1               5                   10

<210> SEQ ID NO 58
<211> LENGTH: 14
<212> TYPE: PRT
<213> ORGANISM: Artificial Sequence
<220> FEATURE:
<223> OTHER INFORMATION: KL-L9PL13A

<400> SEQUENCE: 58

Lys Leu Leu Lys Leu Leu Lys Lys Pro Leu Lys Leu Ala Lys
1               5                   10

<210> SEQ ID NO 59
<211> LENGTH: 14
<212> TYPE: PRT
<213> ORGANISM: Artificial Sequence
<220> FEATURE:
<223> OTHER INFORMATION: KLA-L9P

<400> SEQUENCE: 59

Lys Leu Ala Lys Leu Ala Lys Lys Pro Leu Lys Leu Ala Lys
1               5                   10

<210> SEQ ID NO 60
<211> LENGTH: 5
<212> TYPE: PRT
<213> ORGANISM: Artificial Sequence
<220> FEATURE:
<223> OTHER INFORMATION: Synthetic construct

<400> SEQUENCE: 60

Lys Lys Pro Leu Lys
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic construct

<400> SEQUENCE: 61

Lys Leu Asp Lys Lys
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic construct

<400> SEQUENCE: 62

Gln Phe Pro Val Gly
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic construct

<400> SEQUENCE: 63

Leu Leu Lys Lys Pro Leu Lys Leu Leu
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic construct

<400> SEQUENCE: 64

Leu Leu Lys Leu Asp Lys Lys Leu Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic construct

<400> SEQUENCE: 65

Gly Leu Gln Phe Pro Val Gly Arg Val
1               5

<210> SEQ ID NO 66
<211> LENGTH: 11
<212> TYPE: PRT
<213> ORGANISM: Artificial Sequence
<220> FEATURE:
<223> OTHER INFORMATION: Synthetic construct

<400> SEQUENCE: 66

Lys Leu Leu Lys Lys Pro Leu Lys Leu Leu Lys
1               5                   10

-continued

<210> SEQ ID NO 67
<211> LENGTH: 11
<212> TYPE: PRT
<213> ORGANISM: Artificial Sequence
<220> FEATURE:
<223> OTHER INFORMATION: Synthetic construct

<400> SEQUENCE: 67

Lys Leu Leu Lys Leu Asp Lys Lys Leu Leu Lys
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic construct

<400> SEQUENCE: 68

Ala Gly Leu Gln Phe Pro Val Gly Arg Val His
1               5                   10

<210> SEQ ID NO 69
<211> LENGTH: 6
<212> TYPE: PRT
<213> ORGANISM: Artificial Sequence
<220> FEATURE:
<223> OTHER INFORMATION: Synthetic construct

<400> SEQUENCE: 69

Leu Lys Pro Pro Lys Lys
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic construct

<400> SEQUENCE: 70

Leu Leu Lys Pro Pro Lys Lys Leu
1               5

<210> SEQ ID NO 71
<211> LENGTH: 10
<212> TYPE: PRT
<213> ORGANISM: Artificial Sequence
<220> FEATURE:
<223> OTHER INFORMATION: Synthetic construct

<400> SEQUENCE: 71

Lys Leu Leu Lys Pro Pro Lys Lys Leu Leu
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic construct

<400> SEQUENCE: 72

Lys Lys Leu Leu Lys Pro Pro Lys Lys Leu Leu Lys
1               5                   10

<210> SEQ ID NO 73

```
<211> LENGTH: 4
<212> TYPE: PRT
<213> ORGANISM: Artificial Sequence
<220> FEATURE:
<223> OTHER INFORMATION: Synthetic construct

<400> SEQUENCE: 73

Lys Pro Leu Lys
1

<210> SEQ ID NO 74
<211> LENGTH: 6
<212> TYPE: PRT
<213> ORGANISM: Artificial Sequence
<220> FEATURE:
<223> OTHER INFORMATION: Synthetic construct

<400> SEQUENCE: 74

Leu Lys Lys Pro Leu Lys
1               5

<210> SEQ ID NO 75
<211> LENGTH: 7
<212> TYPE: PRT
<213> ORGANISM: Artificial Sequence
<220> FEATURE:
<223> OTHER INFORMATION: LLKKPLK

<400> SEQUENCE: 75

Leu Leu Lys Lys Pro Leu Lys
1               5
```

BROKEN OR FOLDED HELICAL PEPTIDE OR PEPTIDE ANALOG EXHIBITING ANTIMICROBIAL ACTIVITY AGAINST GRAM-NEGATIVE BACTERIA, AND USE THEREOF

CROSS-REFERENCE TO RELATED APPLICATIONS

This application is a U.S. national phase under the provisions of 35 U.S.C. § 371 of International Patent Application No. PCT/KR16/10408 filed Sep. 19, 2016, which in turn claims priority of Korean Patent Application No. 10-2015-0131555 filed Sep. 17, 2015 and Korean Patent Application No. 10-2016-0119524 filed Sep. 19, 2016. The disclosures of such international patent application and Korean priority patent applications are hereby incorporated herein by reference in their respective entireties, for all purposes.

TECHNICAL FIELD

The present invention relates to a broken or kinked helical peptide or peptide analogue and the use thereof, and more particularly to a Gram-negative bacterial membrane-penetrating peptide or peptide analogue wherein an amphipathic alpha-helical peptide composed of hydrophobic amino acids and hydrophilic amino acids has a kinked structure, or an antimicrobial composition employing the specific activity of the peptide against the Gram-negative bacterial membrane, or an antimicrobial composition for co-administration, or a conjugate comprising a drug linked to the peptide or peptide analogue, or an antibiotic comprising the same.

BACKGROUND ART

As the proportion of resistant bacteria against antimicrobial drugs, which are classified into Gram-positive bacteria and Gram-negative bacteria, has increased gradually, it will not be long before bacteria that are resistant to all existing drugs will spread. Hospital-acquired infections caused by such resistant bacteria are most serious. For example, in 2014, the number of hospital-acquired infection patients in the US alone was about 1.7 million, and the number of deaths caused by hospital-acquired infections reached about 100,000. This number of deaths is more than the sum of the number of breast cancer deaths, which account for the largest proportion of female deaths in the US, and the number of prostate cancer deaths which account for the largest proportion of male deaths in the US.

In order to overcome these resistant bacteria, new antimicrobial agents must be continuously introduced. Fortunately, new drugs against Gram-positive bacteria have also been introduced in the 2000s. However, antimicrobial therapeutic agents against Gram-negative bacteria have not emerged since the 1980s. Furthermore, since there is no candidate compound in the pipeline for developing a new drug capable of suppressing Gram-negative bacteria, it takes at least 10 to 20 years to develop a new drug.

Although new antibiotics against Gram-negative bacteria have to be developed very quickly, there is no medicine against Gram-negative bacteria, and thus special measures against Gram-negative bacteria are needed for the disease. Repositioning or repurposing efforts have been attempted to screen all drugs, developed for other uses approved by the FDA so far, against Gram-negative bacteria and to use them as new antibiotics. It was reported that 42 of 772 drugs are effective against Gram-positive bacterial and two of them are effective against Gram-negative bacteria. However, these two drugs are effective at very high concentrations. Thus, in view of the toxicity of compounds, etc., it appears that there is no repositionable drug selected by screening, which can act against Gram-negative bacteria.

In this regard, there are a significantly large number of drugs against Gram-positive bacteria, whereas there are little drugs against Gram-negative bacteria. This is believed to be because antibiotic candidates cannot pass through the outer membrane of Gram-negative bacteria.

Since the outer membrane starting with the LPS (lipopolysaccharide) layer possesses both hydrophilic and hydrophobic properties by the LPS layer, most low-molecular-weight drugs cannot pass through the membrane freely. It is known that most of the antibiotics that are not effective against Gram-negative bacteria while being effective against Gram-positive bacteria cannot pass through the outer membrane. Representative drugs include Linezolid, Cloxacillin and the like.

Therefore, the outer membrane of Gram-negative bacteria is a major target for developing new drugs, and a compound capable of degrading or weakening the outer membrane can be used as a therapeutic agent against Gram-negative bacteria. In fact, many kinds of antimicrobial peptides (AMPS) have an antimicrobial effect as a mechanism of decomposing this membrane. A method of introducing antibiotics, which could not pass through the membrane, into bacteria by using such AMPS, has been considered. This hypothesis can be verified by the synergistic effect of co-administration of an antimicrobial peptide and an antibiotic.

However, the previously reported synergistic effects of co-administration were false-positive due to errors in experimental methods, and there was no synergy between an antimicrobial peptide and an antibiotic. In other words, it was proved that the method of increasing the synergy of existing antibiotics by use of antimicrobial peptides that degrade the membrane does not work as expected. The fact that the penetration of an antibiotic into bacteria by membrane degradation caused by an antimicrobial peptide has no synergy may probably be due to time-lag mismatch. This fact may be because antimicrobial peptides degrade the membrane very rapidly, while most antibiotics show efficacy at a rate slower than the degradation rate of the membrane.

Therefore, it is considered that, rather than peptides that rapidly degrade and damage the bacterial membrane, peptides, which can enter bacteria through the bacterial membrane without damaging the membrane or can loosen the membrane by activating the membrane itself, can effectively give synergistic effects. Namely, it is considered that antibiotics, which could not pass through the membrane due to the rigidity of the membrane, can pass through the membrane and can exhibit synergistic effects.

Under this technical background, the present inventors have found Gram-negative bacterial membrane-activating peptides or peptide analogues having the ability to loosen the outer membrane of Gram-negative bacterial by acting specifically on only the membrane, and the use thereof, thereby completing the present invention.

DISCLOSURE OF INVENTION

Technical Problem

It is an object of the present invention to provide a peptide or peptide analogue having an alpha-helical structure wherein one or more hydrophobic amino acids of an amphipathic alpha-helical peptide composed of hydrophobic amino acids and hydrophilic amino acids are kinked or broken by substitution.

Another object of the present invention is to provide an antimicrobial composition for co-administration, comprising the above-described peptide or peptide analogue.

Still another object of the present invention is to provide a conjugate comprising: a peptide or peptide analogue; and a drug linked to the peptide.

Technical Solution

To achieve the above object, the present invention provides a Gram-negative bacterial membrane-penetrating peptide or peptide analogue wherein an amphipathic alpha-helical peptide composed of hydrophobic amino acids and hydrophilic amino acids has a kinked structure, the peptide or peptide analogue comprising:

i) an alpha-helical structure wherein one or more hydrophobic amino acids of the amphipathic alpha-helical peptide or peptide analogue are kinked by substitution with one or more selected from the group consisting of proline (P), aspartic acid (D), asparagine (N), glutamic acid (E), glutamine (Q), D-form amino acids thereof, and derivatives thereof; or ii) an alpha-helical structure wherein two or more amino acids of the amphipathic alpha-helical peptide are kinked by linkage through a disulfide bond, a carbon-carbon bond, a maleimide bond or an amide bond at one or more positions selected from the group consisting of i, i+3, i+4, i+7, i+8, i+10 and i+11 (wherein i is an integer).

The present invention also provides a peptide or peptide analogue having a kinked alpha-helical structure by substitution of the hydrophobic portion of an amphipathic antibiotic peptide (for example, buforin 5-21) with proline (P), aspartic acid (D), asparagine (N), glutamic acid (E), or glutamine (Q).

The present invention also provides an antimicrobial composition for co-administration, comprising the above-described peptide or peptide analogue.

The present invention also provides a conjugate comprising: the above-described peptide or peptide analogue; and a drug linked to the peptide.

The present invention also provides an antibiotic comprising the above-described composition or conjugate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
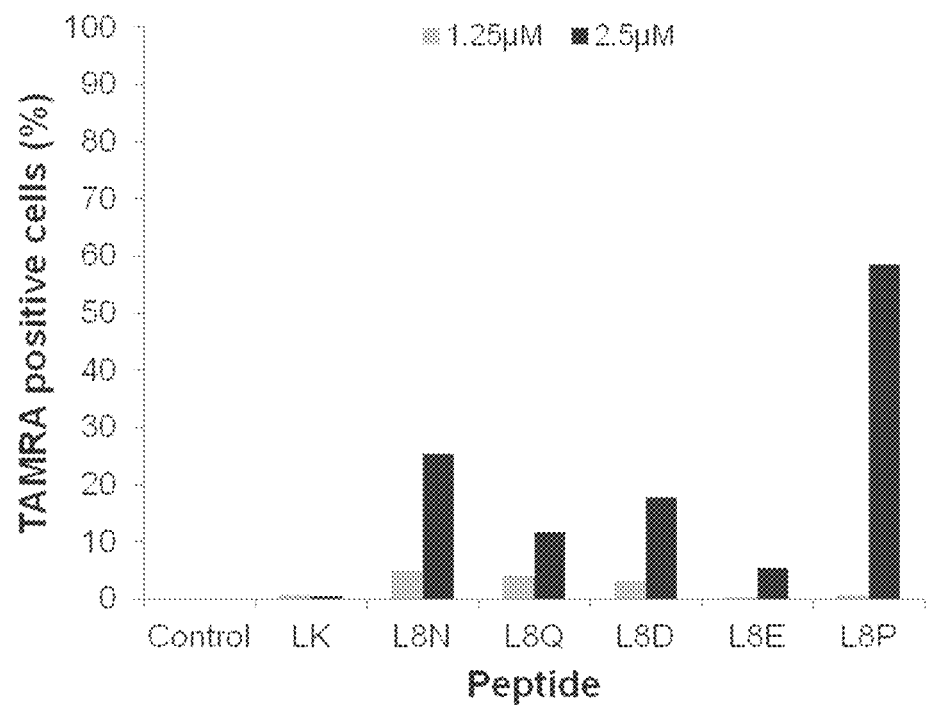
FIG. 1 shows the results of FACS performed to confirm whether peptides according to the present invention actually penetrate the outer membrane of Gram-negative bacteria, after labeling five mutant peptides (P, N, D, Q and E) with the fluorescent label TAMRA.

Until now, several antimicrobial peptides (AMPS) capable of eradicating Gram-negative bacteria have been known. However, these peptides mostly eradiate pathogenic bacteria by a mechanism that degrades the cell wall of the bacteria. These peptides degrade not only the cell wall of Gram-negative bacteria, but also eukaryotic cells that are host cells, and thus the use of these peptides as antibiotics cause many side effects. However, when these AMPS are mutated in various forms, the nature thereof changes little by little. Among them, specific mutants have a reduced ability to degrade the cell wall of eukaryotic cells, and also have the ability to pass specifically through the membrane of Gram-negative bacteria or activate only the outer membrane, thus exhibiting only properties specific for Gram-negative bacteria.

Accordingly, the present inventors have attempted to find peptides that do not hemolyze or penetrate host eukaryotic cells while retaining the property of penetrating Gram-negative bacterial cells by continuously mutating peptides having an amphipathic helical structure.

The compound, which was developed in the early 1950s but is not frequently used as a therapeutic agent against Gram-negative bacteria due to its severe toxicity, is colistin, a polymyxin-based antibiotic. Colistin is a cyclic amphipathic peptide which is rich in cations and has long carbon chains at one side. Regarding the reaction mechanism of colistin, it is known that colistin recognizes the LPS lipid layer present in the outer membrane of Gram-negative bacteria, enters the outer membrane to loosen the outer membrane, and also penetrates the inner membrane by long carbon chain moieties, thereby killing the bacteria. Namely, regarding the mechanism of the colistin antimicrobial peptide, colistin does not rapidly degrade the bacterial membrane, unlike other antimicrobial peptides, but rather can loosen the membrane while staying in the membrane for a long period of time. Thus, it was reported that the synergy of colistin with several low-molecular antibiotic molecules could be actually observed. This colistin is used as a golden standard to loosen the outer membrane, and is relatively less active for the membrane of eukaryotic cells other than Gram-negative bacteria. The present invention is intended to find amphipathic peptide mutants whose ability to stimulate the outer membrane is similar to that of colistin, but which are less toxic and have a maximized ability to disrupt the outer membrane.

In various mutation studies on some mutant peptides having a kinked or broken structure capable of eradiating Gram-negative bacteria while having a reduced alpha-helical content, it was found that when the most sensitive portion of the hydrophobic side of the peptide is substituted with a hydrophilic amino acid residue, the activity of the peptide against host cells can be eliminated due to the kinked or broken structure of the alpha helix so that the side effects of the peptide can be minimized. In addition, it was found that some mutant peptides with a kinked or broken structure can degrade or pass through the membrane of the gram-negative bacterium *E. coli* to enter the bacterium, and thus can kill Gram-negative bacteria or at least loosen the membrane.

Based on these findings, in one aspect, the present invention is directed to a Gram-negative bacterial membrane-penetrating peptide or peptide analogue having a kinked or broken alpha-helical structure by substitution of one or more hydrophobic amino acids of an amphipathic alpha-helical peptide composed of hydrophobic amino acids and hydrophilic amino acids. In this case, the substituted hydrophobic amino acids are one or more selected from the group consisting of proline (P), aspartic acid (D), asparagine (N), glutamic acid (E), glutamine (Q), D-form amino acids thereof, and derivatives thereof (For example, B (KL-L9P) and C (LK-L8D) structures in FIG. 16).

Figure 16:
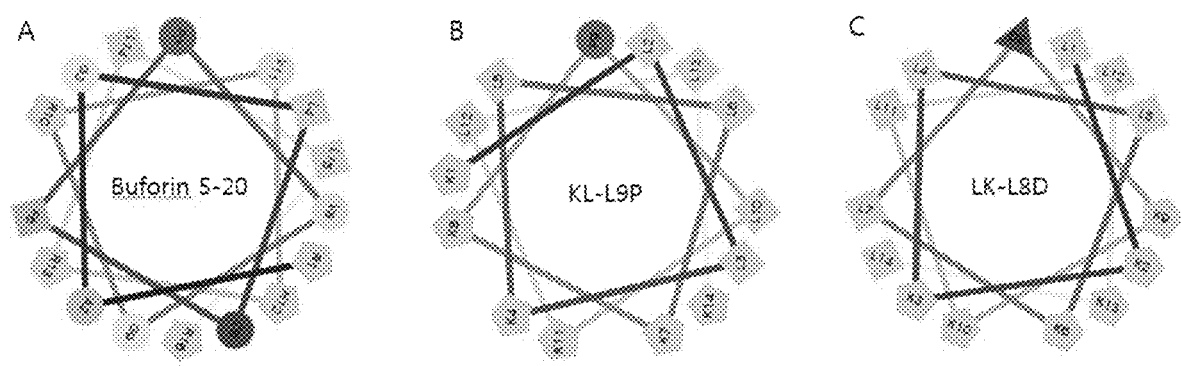
FIG. 16 depicts wheel diagrams of three peptides showing synergistic effects with antibiotics due to their activity against the outer membrane of Gram-negative bacteria in the present invention. Generally, it shows a structure in which the hydrophobic side of the amphipathic peptide is damaged and kinked by proline (see FIG. 15).

In some embodiments, the present invention is directed to a peptide or peptide analogue having an alpha-helical structure wherein the hydrophobic portion of a naturally occurring amphipathic peptide (for example, buforin 5-21) is kinked by substitution with proline (P), aspartic acid (D), asparagine (N), glutamic acid (E), or glutamine (Q) (structure A in FIG. 16). As used herein, the term "kinked" may be used as a same or interchangeable meaning with the term "bent or broken" through the specification. The "kinked" structure may be a structure formed by substitution of one or more hydrophobic amino acids of the amphipathic alpha-helical peptide composed of hydrophobic amino acids and hydrophilic amino acids, or a structure wherein the alpha-helix is bent with respect to the amino acid-substituted portion in the amphipathic alpha-helical peptide.

In this case, the substituted amino acids may be one or more selected from the group consisting of proline (P), aspartic acid (D), asparagine (N), glutamic acid (E), glutamine (Q), D-form amino acids thereof, and derivatives thereof.

In particular, it was found that when a hydrophobic side composed of hydrophobic amino acids is mutated by proline (P), thereby constructing a peptide, the constructed peptide can specifically activate the membrane without damaging the membrane, unlike the general property of AMP. Namely, it was expected that peptides according to the present invention would enter the membrane or loosen the membrane so that other compounds with low-molecular weight (e.g. small molecule) would easily penetrate bacteria. It was expected that the use of these peptides would give synergistic effects with antibiotics, like colistin that loosens the membrane, and would also make it possible to reposition therapeutic drugs that are used for other purposes.

Figure 15:
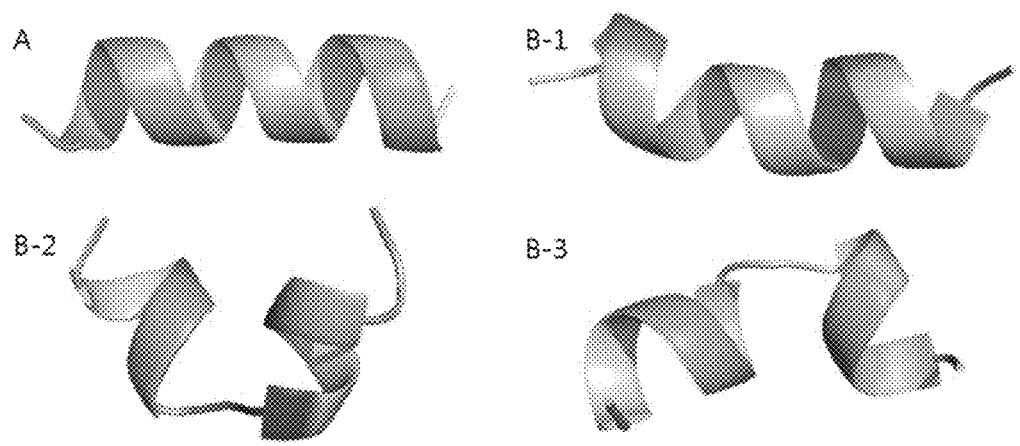
FIG. 15 compares peptides having an amphipathic alpha-helical structure with peptides having a kinked or broken structure according to the present invention.

In connection with this, A in FIG. 15 corresponds to an amphipathic alpha-helical KL peptide having a non-kinked or non-broken structure, B-1 shows a KL-L9P formed by substituting L at position 9 with proline, B-2 shows an LK-L7PL8P formed by substituting L at positions 7 and 8 with proline, and B-3 shows an LK-L8D formed by substituting L at position 8 with aspartic acid.

In addition, as shown in FIG. 16, an amphipathic alpha-helical peptide having a non-kinked or non-broken structure retains a kind of completely cylindrical structure, whereas a kinked or broken peptide may have a bent shape in the amino acid-substituted portion.

Among the above-illustrated amino acids, the D-form amino acids are amino acids that do not naturally occur, unlike L-form amino acids, and substitution with a D-form amino acid may provide a peptide which is diastereomeric with the original peptide. When a peptide is substituted with a D-form amino acid, the alpha-helix can further be broken while the amino acid sequence of the peptide is changed, and thus the toxicity of the peptide for host cells can further be reduced and the peptide can be protected from attack by natural enzymes so that the in vivo half-life thereof can increase.

The amino acid derivatives as illustrated above may contain various protecting groups on the amino acids. For example, a derivative of proline may be azetidine-2 carboxylic acid, homoproline, hydroxyproline, alpha methyl proline, or 4-fluoroproline, and a derivative of glutamic acid may be alpha amino adipic acid, gamma hydroxyl glutamic acid, 2-amino heptanedioic acid, or alpha amino suberic acid, but are not limited thereto. The definition and exemplification as described above can be equally applied to the derivatives used herein.

In addition, the Gram-negative bacterial membrane-penetrating peptide according to the present invention has an alpha-helical structure wherein two or more amino acids of an amphipathic alpha-helical peptide are linked and kinked by a disulfide bond, a carbon-carbon bond, a maleimide bond or an amide bond at one or more positions selected from the group consisting of i, i+3, i+4, i+7, i+8, i+10 and i+11 (wherein i is an integer). The staple structure is disclosed in the international patent publication No. WO2016/085280 whose application was filed by the present inventors, the contents of which are incorporated herein by reference.

The peptide or peptide analogue may exhibit any one of the following characteristics:

i) it has activity against Gram-negative bacteria without having hemolytic activity against host cells or activity against Gram-positive bacteria;

ii) it is capable of binding to an LPS layer on the surface of a Gram-negative bacterial outer membrane;

iii) it is capable of binding to an LPS layer on the surface of a Gram-negative bacterial outer membrane while entering the outer membrane and staying only in the outer membrane;

iv) it has the property of penetrating a Gram-negative bacterial outer membrane and staying only in the outer membrane while having no ability to degrade the outer or inner membrane;

v) among the amphipathic peptides according to the present invention, an amphipathic alpha-helical peptide wherein the hydrophobic amino acid at a specific position, for example, one or more positions selected from positions 6, 7, 8, 9, 11 and 12 in the N-terminus to C-terminus direction, is substituted with proline (P), aspartic acid (D), asparagine (N), glutamic acid (E), glutamine (Q), D-form amino acids thereof, and derivatives thereof, has a relatively strong hydrophilicity compared to a peptide having the same amino acid composition, for example, a peptide which comprises hydrophilic amino acids and hydrophobic amino acids and in which some amino acids are substituted with proline (P), aspartic acid (D), asparagine (N), glutamic acid (E), glutamine (Q), D-form amino acids thereof, and derivatives thereof.

vi) it has a structure wherein the alpha-helix is kinked by Pro, and the kinked portion is hydrophobic;

vii) the content of positively charged amino acids is 35% (6/16) or more based on the total content of amino acids, or the content of hydrophobic amino acids is 35% (6/16) or more based on the total content of amino acids;

viii) it has no hemolytic activity against host cells and no activity against Gram-positive bacteria; and ix) its activity against Gram-negative bacteria remains weakly (MIC=10-20 µM).

The present invention also encompasses "peptide analogues". The peptide analogues may include analogues wherein an alpha-amino acid side chain or an alpha-amino acid backbone is substituted with one or more other functional groups. Examples of side chain- or backbone-modified peptide analogues include hydroxyproline peptides wherein a pyrrolidine ring is substituted with a hydroxyl group, or N-methylglycine "peptoids".

In one embodiment, the hydrophilic amino acids of the amphipathic alpha-helical peptide may comprise one or more selected from a positively charged amino acid group consisting of arginine, lysine, and histidine. In addition, the hydrophobic amino acids may be one or more selected from the group consisting of leucine, valine, tryptophan, phenylalanine, tyrosine, isoleucine, D-form amino acids thereof, and derivatives thereof.

Among the above-illustrated amino acids, D-form amino acids are amino acids that do not naturally occur as mentioned above. Substitution with a D-form amino acid can provide a peptide which is diastereomeric with the original peptide.

In one embodiment, the amphipathic alpha-helical peptide may comprise a five-amino-acid sequence represented by the following formula (1) or (1-1), the reverse sequence thereof, or a sequence containing the same repeatedly:

XXZYX (1)

XYZYY (1-1)

wherein X is a hydrophilic amino acid; Y is a hydrophobic amino acid; and Z is proline, aspartic acid, asparagine, glutamic acid, glutamine, or a derivative thereof which is an amino acid substituted for a kinked or broken structure. In this case, the hydrophilic amino acid may be arginine, lysine, histidine, or a derivative thereof, and the hydrophobic amino acid may be leucine, valine, tryptophan, phenylalanine, tyrosine, isoleucine, or a derivative thereof.

A specific example of the sequence of the peptide represented by formula (1) or (1-1) may be KKPLK (SEQ ID NO: 60), KLDKK (SEQ ID NO: 61) or QFPVG (SEQ ID NO: 62).

The reverse sequence means a sequence obtained by reading the sequence defined by formula (1) or (1-1) (which is read in the 5' to 3' direction) in the 3' to 5' direction. For example, the reverse sequence of the five-amino-acid sequence represented by formula (1) may be XYZXX.

The "sequence containing the same repeatedly" may mean a sequence comprising the sequence of formula (1) or (1-1) repeatedly several times, for example, 2 to 10 times, preferably 2 to 5 times, in the 5' to 3' direction. For example, when the sequence defined by formula (1) or (1-1) is repeated twice, the sequence containing the same repeatedly may comprise a sequence of XXZYXXXZYX.

In some cases, the amino acid sequence may be constructed in a dimeric or tetermeric form.

In addition, the amphipathic alpha-helical peptide may comprise a seven-amino-acid sequence represented by the following formula (2) or (2-1), the reverse sequence thereof, or a sequence containing the same repeatedly:

YXXZYXY (2)

YXYZYYX (2-1)

wherein X, Y and Z are the same as defined in formula (1).

A specific example of the sequence of the peptide represented by formula (2) or (2-1) may be LKKPLKL or LKLDKKL.

In addition, the amphipathic alpha-helical peptide may comprise a nine-amino-acid sequence represented by the following formula (3) or (3-1), the reverse sequence thereof, or a sequence containing the same repeatedly:

YYXXZYXYY (3)

YYXYZYYXY (3-1)

wherein X, Y and Z are the same as defined in formula (1).

A specific example of the sequence of the peptide represented by formula (3) or (3-1) may be LLKKPLKLL (SEQ ID NO: 63), LLKLDKKLL (SEQ ID NO: 64) or GLQFPVGRV (SEQ ID NO: 65).

In addition, the amphipathic alpha-helical peptide may comprise an eleven-amino-acid sequence represented by the following formula (4) or (4-1), the reverse sequence thereof, or a sequence containing the same repeatedly:

XYYXXZYXYYX (4)

YYYXYZYYXYX (4-1)

wherein X, Y and Z are the same as defined in formula (1).

A specific example of the sequence of the peptide represented by formula (4) or (4-1) may be KLLKKPLKLLK (SEQ ID NO: 66), KLLKLDKKLLK (SEQ ID NO: 67) or AGLQFPVGRVH (SEQ ID NO: 68).

In addition, the amphipathic alpha-helical peptide may comprise a six-amino-acid sequence represented by the following formula (5), the reverse sequence thereof, or a sequence containing the same repeatedly:

YXZZXX (5)

wherein X, Y and Z are the same as defined in formula (1).

A specific example of the sequence of the peptide represented by formula (5) may be LKPPKK (SEQ ID NO: 69).

In addition, the amphipathic alpha-helical peptide may comprise an eight-amino-acid sequence represented by the following formula (6), the reverse sequence thereof, or a sequence containing the same repeatedly:

YYXZZXXY    (6)

wherein X, Y and Z are the same as defined in formula (1).

A specific example of the sequence of the peptide represented by formula (6) may be LLKPPKKL (SEQ ID NO: 70).

In addition, the amphipathic alpha-helical peptide may comprise a ten-amino-acid sequence represented by the following formula (7), the reverse sequence thereof, or a sequence containing the same repeatedly:

XYYXZZXXYY    (7)

wherein X, Y and Z are the same as defined formula (1).

A specific example of the sequence of the peptide represented by formula (7) may be KLLKPPKKLL (SEQ ID NO: 71).

In addition, the amphipathic alpha-helical peptide may comprise a twelve-amino-acid sequence represented by the following formula (8), the reverse sequence thereof, or a sequence containing the same repeatedly:

XXYYXZZXXYYX    (8)

wherein X, Y and Z are the same as defined in formula (1).

A specific example of the sequence of the peptide represented by formula (8) may be KKLLKPPKKLLK (SEQ ID NO: 72).

In one embodiment, the amphipathic alpha-helical peptide may be composed of 12-20, preferably 12-18, more preferably 12-16, even more preferably 12-14 amino acids comprising hydrophobic amino acids and hydrophilic amino acids.

In some cases, the amphipathic alpha-helical peptide may comprise one or more residues, selected from the group consisting of positively charged arginine, lysine and histidine, in an amount equal to 35% or more of the total amino acids of the peptide.

In addition, the amphipathic alpha-helical peptide may comprise one or more hydrophobic amino acid residues, selected from the group consisting of leucine, tryptophan, valine, phenylalanine, tyrosine, and isoleucine, in an amount equal to 35% or more of the total amino acids of the peptide.

In one embodiment, the amphipathic alpha-helical peptide may comprise a sequence represented by the following SEQ ID NO: 1 or 2, the reverse sequence thereof, or a sequence containing the same repeatedly:

KLLKL    (SEQ ID NO: 1)

LKKLL.    (SEQ ID NO: 2)

In this regard, an amino acid sequence of (LK)n or (KL)n may additionally be bound upstream of SEQ ID NO: 1 or 2, or an amino acid sequence of (LK)m or (KL)m may be bound downstream of SEQ ID NO: 1 or 2. Here, n or m may be an integer ranging from 0 to 2.

In one embodiment, the amphipathic alpha-helical peptide may comprise a sequence represented by the following SEQ ID NO: 3 or 4, the reverse sequence thereof, or a sequence containing the same repeatedly:

LKKLLKL    (SEQ ID NO: 3)

KLLKLLK.    (SEQ ID NO: 4)

In this regard, an amino acid sequence of (LK)n or (KL)n may additionally be bound upstream of SEQ ID NO: 3 or 4, or an amino acid sequence of (LK)m or (KL)m may be bound downstream of SEQ ID NO: 3 or 4. Here, n or m may be an integer ranging from 0 to 2.

In order to form a kinked or broken peptide structure in this amphipathic alpha-helical peptide, the amino acid at one or more positions selected from the group consisting of positions 6, 7, 8, 9, 11 and 12 in the N-terminus to C-terminus direction may be substituted. In this case, the substituted amino acid may be proline, aspartic acid, or a derivative thereof.

In an embodiment of the present invention, the amphipathic alpha-helical peptide may be LKKLLKLLKKLLKL (SEQ ID NO: 5) or KLLKLLKKLLKLLK (SEQ ID NO: 6), and may comprise a substituted amino acid for a kinked structure at positions 7 and 8 (leucine) of SEQ ID NO: 5 or position 9 of SEQ ID NO: 6. In this case, the substituted amino acid may comprise an amino acid sequence substituted with proline, aspartic acid, asparagine, glutamic acid, glutamine, or derivatives thereof, preferably proline, aspartic acid, or derivatives thereof.

In still another aspect, the present invention is directed to an antimicrobial composition for co-administration, comprising the peptide or peptide analogue. In particular, the present invention is directed to an antimicrobial composition against Gram-negative bacteria or an antimicrobial composition for co-administration. Specifically, the present invention is directed to a method for preventing or treating infectious diseases caused by microorganisms, comprising administering the composition. In a further aspect, the present invention is directed to an antibiotic comprising the composition.

In this regard, the microorganism means a pathogenic microorganism or resistant bacterium, preferably a Gram-negative pathogenic microorganism or resistant bacterium. As used herein, the term "preventing" refers to all actions that inhibit infectious diseases caused by the pathogenic microorganism or resistant bacterium or delay the onset of infectious diseases caused by the pathogenic microorganism or resistant bacterium by administering the composition. As used herein, the term "treatment" refers to any action resulting in improvements in symptoms of infectious diseases caused by the pathogenic microorganism or resistant bacterium or the beneficial alteration of infectious diseases caused by the pathogenic microorganism or resistant bacterium owing to the administration of the composition.

The composition may further comprise a pharmaceutically acceptable carrier. As used herein, the term "pharmaceutically acceptable carrier" refers to a pharmaceutically acceptable material, composition or vehicle, such as a liquid or solid filler, diluent, excipient, solvent or encapsulating material, which is involved in carrying or transporting a composition or component of interest from one organ, or portion of the body to another organ, or portion of the body. The composition of the present invention may further comprise a pharmaceutically acceptable carrier, excipient or diluent besides the above-mentioned active ingredients for the purpose of administration thereof. Examples of said carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oils.

In addition, the composition according to the present invention can be formulated according to a conventional method. For example, it may be formulated in the form of powders, granules, tablets, capsules, suspensions, emulsions, syrups, aerosols, agents for oral and external applications, suppositories, or sterile injection solutions. Specifically, the pharmaceutical composition according to the present invention is formulated using diluents or excipients, such as fillers, extenders, binders, wetting agents, disintegrants or surfactants, which are commonly used. Solid formulations for oral administration include tablets, pills, powders, granules, capsules, etc., but are not limited thereto. Such solid Formulations are prepared by mixing the composition of present invention with at least one excipient, such as starch, calcium carbonate, sucrose, lactose, gelatin, etc. In addition to simple expedients, lubricants such as magnesium stearate, talc, etc. may also be added. Liquid Formulations for oral administration include suspensions, internal solutions, emulsions, syrups, etc., but are not limited thereto, and may be prepared by adding simple diluents, e.g., water and liquid paraffin, as well as various excipients, e.g., wetting agents, sweeteners, aromatics, preservatives, etc. Formulations for parenteral administration include sterilized aqueous solutions, non-aqueous solvents, suspensions, emulsions, lyophilized agents, and suppositories. Non-aqueous solvents and suspensions may be prepared using propylene glycol, polyethylene glycol, vegetable oils such as olive oil, or injectable esters such as ethyloleate. As a base for suppositories, Witepsol, Macrogol, Tween 61, cacao fat, laurin fat, glycerogelatin, etc. may be used.

The composition according to the present invention may be administered orally, or parenterally (for example, intravenously, subcutaneously, intraperitoneally, or topically) according to a desired purpose. The preferred dosage of the composition of the present invention varies depending on various factors, including the patient's condition and weight, the severity of disease, the type of drug, the route and period of administration, but can be suitably determined by a person skilled in the art. The composition may be administered in a single dose or in multiple doses per day, if necessary. The composition of the present invention may be used alone or in combination of surgery, hormone treatment, drug treatment, and methods using a biological response modifier in order to prevent or treat infectious diseases caused by pathogenic bacterium or resistant bacterium.

As used herein, the term "co-administration" may be used interchangeably with concurrent administration. The mode of co-administration may include administering the peptide or peptide analogue concurrently with other compounds, or administering the peptide or peptide analogue separately from other compounds. In this regard, the peptide or peptide analogue according to the present invention may be co-administered with one or more selected from the group consisting of a hydrophobic compound having a log P (partition coefficient) value of 0.19 or higher, a compound positively charged under physiological pH conditions, and colistin.

The hydrophobic compound having a log P (partition coefficient) value of 0.19 or higher may be, for example, Cloxacillin, linezolid, resveratrol, curcumin, quercetin, simvastatin, lovastatin, mevastatin, catechin, or thymol, but is not limited thereto.

The compound positively charged under physiological pH conditions, for example, at pH 7.3-7.4, may be, for example, erythromycin, rifampicin, colistin, polymyxin B, or nicotine, but is not limited thereto.

The compound negatively charged under physiological pH conditions, for example, at pH 7.3-7.4, may be, for example, ibuprofen, atorvastatin, fluvastatin, pravastatin, carprofen, trans-ferulic acid, or bromfenac, but is not limited thereto.

In one embodiment, a compound that exhibits a synergistic effect when co-administered with the peptide or peptide analogue according to the present invention may be, for example, linezolid, erythromycin, ibuprofen, simvastatin, curcumin, or resveratrol. This compound exhibits an antimicrobial effect even at significantly lower concentrations, compared to when the effect resulting from a plurality of peptides or peptide derivatives or compounds to be co-administered is simply added.

In yet another aspect, the present invention is directed to a conjugate comprising: the peptide or peptide analogue; and a drug linked to the peptide or peptide analogue. The present invention is also directed to an antibiotic comprising the conjugate.

The drug may be a hydrophobic compound having a log P (partition coefficient) value of 0.19 or higher, a compound positively charged under physiological pH conditions, or colistin. The definition of each component is the same as mentioned above.

The peptide or peptide analogue and the drug may be linked to each other by, for example, a non-covalent bond or a covalent bond. The non-covalent bond may be one or more selected from the group consisting of, for example, a hydrogen bond, an electrostatic interaction, a hydrophobic interaction, a van der Waals interaction, a pi-pi interaction, and a cation-pi interaction. The covalent bond may be either a degradable bond or a non-degradable bond. The degradable bond may be a disulfide bond, an acid-degradable bond, an ester bond, an anhydride bond, a biodegradable bond, or an enzyme-degradable bond, but is not limited thereto. The non-degradable bond may be either an amide bond or a phosphate bond, but is not limited thereto.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Synthesis of Variants of Amphipathic LK Peptide and Selection of Gram-Negative Bacterial Membrane-Specific Peptides There are many antimicrobial peptides (AMPS) in nature. These peptides are mainly peptides that are produced for primary immune responses in the immune systems of higher animals, and the kinds and shapes thereof are also diverse. In recent years, as the new in vivo functions of these antimicrobial peptides have been found, interest in these antimicrobial peptides has increased continuously. However, the actual use of these antimicrobial peptides as antimicrobial agents has not yet been reported. The reasons why these AMPS have not been used as drugs are because the ability of these peptides to kill pathogenic bacteria is excessively lower than that of other low-molecular antimicrobial substances, the production cost of these peptides is higher than that of low-molecular antimicrobial substances, and these antimicrobial peptides have a side effect that can damage host eukaryotic cells.

The present inventors have made efforts to improve the above-described three reasons in order to actually use AMPs as antimicrobial agents. Many naturally occurring AMPs have evolved over many years and have undergone many mutation processes so that their amino acid sequences would maximize the properties of AMPs. In view of this fact, it appeared that it would not be easy to enhance the ability of these naturally occurring peptides or to give selectivity to these peptides. For this reason, the present inventors have attempted to solve the above-described three difficulties by inducing various mutants from the model peptide LK peptide mimicking the naturally occurring AMP, observing changes in the ability of the mutants, and deriving improved peptides, rather than improving the ability of the naturally occurring AMP.

In one effort, the present inventors have performed various mutation processes after selecting amphipathic alpha-helical peptide composed of 14 or 16 amino acids. This is because amphipathic characteristics and alpha-helices have been observed in many naturally occurring AMPs. Another reason why this peptide was selected is because the LK peptide is composed of 14 to 16 amino acids, the economic burden of making the peptide is less than that of naturally occurring peptides. It is a means for solving the second reason. The present inventors first made an effort to solve the third reason. This is because, even if the activity of the peptide against pathogenic bacteria (first reason) is increased, when the peptide is toxic to host eukaryotic cells without selectivity, the effort to increase the activity may come to nothing. In fact, in view of the characteristics of drugs that are frequently used, drugs that may be used at high concentrations due to their high selectivity or therapeutic window (therapeutic index) without side effects can be good new drugs, although it is also important that the drugs have high efficacy. In particular, this consideration should be emphasized for antimicrobial peptides. This is because the mechanism of action of antimicrobial peptides is mainly to disrupt the membrane of pathogenic bacteria, and this ability can also disrupt the wall of host eukaryotic cells.

Since the model peptide that is used in the present invention has the ability to kill host eukaryotic cells together with antimicrobial ability, a first mutation was attempted to reduce the ability to kill host eukaryotic cells. Since the LK peptide is composed of L on the hydrophobic side and K on the hydrophilic side, inducing site-directed mutagenesis thereof is very easy. After site-directed substitution with A, hemolytic activity against red blood cells was examined. When L at position 8 was substituted with A, hemolytic activity was reduced to the greatest extent. For this reason, this L was substituted with other amino acids in order to find an amino acid that minimizes hemolytic activity. It was found that when N (asparagine) was introduced into position 8 (hereinafter referred to as N mutation), hemolytic activity decreased 8,000-fold compared to that of the non-mutated peptide. Furthermore, the N mutation could eradiate *E. coli* even at a 8-fold diluted concentration, indicating that an increase in selectivity of 64,000-fold was obtained by a single mutation.

Although the mechanism of action of the N mutation has not yet been clearly found, it is believed that, because of the bent shape of the helical peptide which is changed temporarily by the N mutation, the peptide can more easily disrupt the membrane of Gram-negative bacteria while its ability to disrupt eukaryotic cells is eliminated. In addition to the ability of AMP to disrupt the membrane, there is another reason why the N mutation peptide has better antimicrobial activity against Gram-negative bacteria. Namely, the N mutation peptide can enter bacteria by a mechanism that activates the membrane, so that it can bind to a substance in the bacteria and suppress the metabolism of the pathogenic bacteria, thereby killing the bacteria. In fact, the N mutation peptide or the like can strongly bind to a molecule such as DNA or RNA, and this binding can lead to the death of pathogenic bacteria by DNA- or RNA-associated metabolic arrest of the pathogenic bacteria.

The increase in selectivity, which results from the above-described experiment, is obtained under a condition where the hemolytic activity and penetration of the mutated peptide for the cell wall of eukaryotic cells are minimized. Namely, at an increase in selectivity of 64,000-fold, hemolytic activity affects 8,000-fold, and antimicrobial activity against Gram-negative bacteria affects 8-fold. In order to observe the increase in antimicrobial activity caused by this mutation, it is preferable to perform mutations of which hemolytic activity has been greatly reduced, and the results of previous studies indicated that such mutations include five mutations, D, E, N, P and Q. In order to rapidly check the ability to penetrate the cells of pathogenic Gram-negative bacteria, five mutants (L8N, L8Q, L8D, L8E and L8P) were made by changing each amino acid at position 8. Since an already performed experiment indicated that position 8 is most sensitive for the hemolysis of eukaryotic cells, it can be expected that a change at position 8 may cause another change. In order to confirm this, the five mutated peptides were labeled with the fluorescent label TAMRA, and FACS was performed to determine whether these peptides would actually enter Gram-negative bacteria. The results are shown in FIG. 1.

Figure 2:
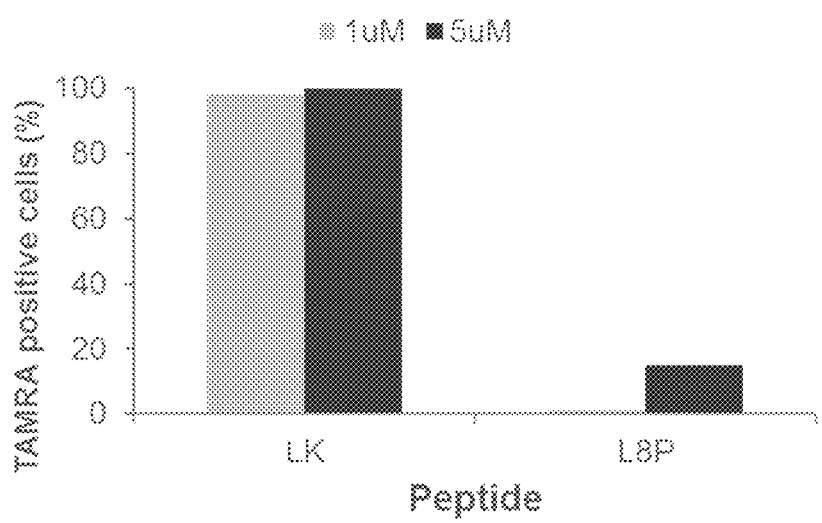
FIG. 2 shows the results of FACS performed to determine the ability of a peptide of the present invention to penetrate MDA MB231 eukaryotic cells.

As expected, the present inventors observed that significantly high concentrations of these mutated peptides could enter Gram-negative bacteria. As shown in FIG. 1, the extent to which the mutated peptides entered Gram-negative bacteria was P>>N=D>Q=E. For P that entered the most, it could be seen that when the peptide was used at a concentration of about 2.5 microM, about 60% of the peptide entered Gram-negative bacteria. It was shown that this mutated peptide cause no hemolysis even at a concentration of at least 100 microM and did not penetrate eukaryotic cells at a concentration of 5 microM in FACS performed using MDA MB231 cells (FIG. 2). In addition, it could be seen that the P-mutant peptide did not enter Gram-positive bacteria (data not shown). In conclusion, the P-mutant peptide can selectively penetrate the cell membrane of Gram-negative bacteria or activate the membrane, and thus the use of the P-mutant peptide makes it possible to selectively deliver a drug to Gram-negative bacteria.

Example 2: Synthesis of Mutated Peptides Using Proline and Selection of Mutant Specific for Gram-Negative Bacterial Membrane (1) Preparation of Pro-Mutant LK and KL Peptide Library Using Solid Phase Peptide Synthesis Method 50 mg of linker amide resin (0.52 g/mmol) was added to a plastic column for synthesis and swollen with DMF for 10 minutes and then 3 mL of 20% piperidine was added thereto, and a deprotection reaction was performed using microwaves. After deprotection, the resulting material was washed three times with DMF, five times with DCM and three times with DMF, and 6 equivalents of amino acid and PyBOP were weighed with an electronic scale and then dissolved in DMF. Amino acid, PyBOP and DIPEA, each corresponding to 6 equivalents, were added to the synthesis column, and an amide bond was formed using microwaves. After coupling, the resulting material was washed three times with DMF, three times with DCM and three times with DMF. One drop of 1% TNBS test solution and one drop of 10% DIPEA solution were dropped onto the resin in order to confirm whether the reaction was completed. After the corresponding amino acid sequence was completely coupled, the N-terminus of the peptide was acetylated using 6 equivalents of HOBt and 6 equivalents of acetic acid anhydride. The peptide synthesized on the resin was detached from the resin by adding 95% v/v TFA, 2.5% v/v distilled water and 2.5% v/v TIS solution to the column and rotating at 800 to 1000 rpm for 2 hours. The broken peptide solution was transferred into a 15 mL Falcon tube, and then TFA was evaporated with nitrogen gas. A crystalline solution (50% v/v n-hexane and 50% v/v diethylether) stored at −20° C. was poured into the 15 mL Falcon tube to a total volume of 10 mL and vortexed for 1 minute so as to form a crystal. After vortexing, the resulting material was centrifuged after balancing with another 15 mL Falcon tube equally weighed in a centrifuge at 4500 rpm at 4° C. for 20 minutes. After the crystalline solution was removed from the crystal, the remaining was vortexed again and centrifuged under the same conditions as described above. The supernatant was removed, and the remaining crystalline solution was evaporated with nitrogen gas, after which the crystal was dissolved in DMSO, filtered through a 0.45 μm filter, and then separated by high-performance liquid chromatography. As the high-performance liquid chromatography column, a C-18 column was used, and as solvents, acetonitrile (0.1% v/v TFA) and distilled water (0.1% v/v TFA) were used. The peptide separated by high-performance liquid chromatography was confirmed by measuring the m/z value using MALDI TOFF. The peptide separated by high-performance liquid chromatography was frozen in a −80° C. freezer for 2 hours, and then freeze-dried. After freeze-drying, in order to remove the remaining TFA, the peptide was dissolved in distilled water, transferred into an e-tube, frozen in at a −80° C. freezer for 2 hours, and further freeze-dried, thereby obtaining peptide powder.

(2) Selection of Gram-Negative Bacterial Membrane-Specific Mutants

As described in Example 1, when the bent alpha-helical peptide was prepared using Pro-mutation, it showed the potential to become a Gram-negative bacterial membrane-specific peptide. In the present invention, a library of peptides having a kinked structure was constructed by substituting Pro for all Lys and Leu residues except the N-terminus or C-terminus of an LK peptide (amino acid sequence: LKKLLKLLKKLLKL; SEQ ID NO: 5) and a KL peptide (amino acid sequence: KLLKLLKKLLKLLK; SEQ ID NO: 6), each consisting of 14 amino acids, and among these mutants, a mutant having the highest specificity for the Gram-negative bacterial membrane was investigated. The N-terminus of the peptides were acetylated and the C-terminus was amidated. The kinked structure can rapidly reduce the alpha-helical content, thereby greatly reducing the toxicity of the peptide against host cells. In addition, because of the potential to show specificity for the Gram-negative bacterial membrane, Pro-mutants were prepared by site-directed mutagenesis. Using the prepared peptides, their MIC for the Gram-negative bacterium *E. coli* and the Gram-positive bacterium *S. aureus* and their hemolytic activity for host cells were examined (Table 1).

TABLE 1

Amino acid sequences of LK peptide Pro-mutants, MIC values for *Escherichia coli* (ATCC 25922) and *Staphylococcus aureus* (ATCC 29213), and MHC values for hemolysis

| Peptide | Sequence | MIC [μM] [a] Against E. coli | MIC [μM] Against S. aureus | MHC [μM] [b] |
|---|---|---|---|---|
| LK | LKKLLKLLKKLLKL (SEQ ID NO: 5) | 20 | 20 | 0.3 |
| LK-L4P | LKKPLKLLKKLLKL (SEQ ID NO: 7) | 5 | 40 | 160 |
| LK-L5P | LKKLPKLLKKLLKL (SEQ ID NO: 8) | 5.0 | 20 | 160 |
| LK-K6P | LKKLLPLLKKLLKL (SEQ ID NO: 9) | 2.5 | 5.0 | 0.60 |
| LK-L7P | LKKLLKPLKKLLKL (SEQ ID NO: 10) | 2.5 | 20 | 160 |
| LK-L8P | LKKLLKLPKKLLKL (SEQ ID NO: 11) | 10 | >40 | 1280 |
| LK-K9P | LKKLLKLLPKLLKL (SEQ ID NO: 12) | 5.0 | 5.0 | 0.60 |
| LK-K10P | LKKLLKLLKPLLKL (SEQ ID NO: 13) | 5.0 | 5.0 | 0.60 |
| LK-L11P | LKKLLKLLKKPLKL (SEQ ID NO: 14) | 5 | >40 | >1280 |
| LK-L12P | LKKLLKLLKKLPKL (SEQ ID NO: 15) | 2.5 | 10 | 160 |

[a] MIC (minimum inhibitory concentration): peptide concentration required to inhibit growth of the representative bacteria by 20%
[b] MHC (minimum hemolytic concentration): peptide concentration required for 10% hemolysis in hRBCs

TABLE 2

Amino acid sequences of KL peptide Pro-mutants, MIC values for *Escherichia coli* (ATCC 25922) and *Staphylococcus aureus* (ATCC 29213), and MHC values for hemolysis

| Peptide | Sequence | MIC [μM] [a] Against E. coli | MIC [μM] Against S. aureus | MHC [μM] [b] |
|---|---|---|---|---|
| KL | KLLKLLKKLLKLLK (SEQ ID NO: 6) | 20 | 20 | 1.25 |
| KL-L2P | KPLKLLKKLLKLLK (SEQ ID NO: 16) | 5 | 20 | 20 |
| KL-L3P | KLPKLLKKLLKLLK (SEQ ID NO: 17) | 10 | 20 | 40 |
| KL-L5P | KLLKPLKKLLKLLK (SEQ ID NO: 18) | 5.0 | 20 | 160 |
| KL-L6P | KLLKLPKKLLKLLK (SEQ ID NO: 19) | 10 | >40 | 1300 |
| KL-K7P | KLLKLLPKLLKLLK (SEQ ID NO: 20) | 2.5 | 5.0 | 1.2 |
| KL-K8P | KLLKLLKPLLKLLK (SEQ ID NO: 21) | 2.5 | 5.0 | 1.2 |

TABLE 2-continued

Amino acid sequences of KL peptide Pro-mutants, MIC values for Escherichia coli (ATCC 25922) and Staphylococcus aureus (ATCC 29213), and MHC values for hemolysis

| Peptide | Sequence | MIC [µM] [a] Against E. coli | MIC [µM] Against S. aureus | MHC [µM] [b] |
|---|---|---|---|---|
| KL-L9P | KLLKLLKKPLKLLK (SEQ ID NO: 22) | 20 | >40 | 1300 |
| KL-L10P | KLLKLLKKLPKLLK (SEQ ID NO: 23) | 2.5 | 20 | 120 |
| KL-L12P | KLLKLLKKLLKPLK (SEQ ID NO: 24) | 2.5 | 20 | 320 |
| KL-L13P | KLLKLLKKLLKLPK (SEQ ID NO: 25) | 5 | 10 | 40 |

[a] MIC (minimum inhibitory concentration): peptide concentration required to inhibit growth of the bacteria by 20%
[b] MHC (minimum hemolytic concentration): peptide concentration required for 10% hemolysis in hRBCs Cytotoxicity for mammalian cells was evaluated by a hemolysis assay. Human red blood cells were washed three times with PBS and suspended in PBS buffer to 5 v/v % to make 5% hematocrit. The peptide was diluted with 2-fold PBS, and then 5% hematocrit was added thereto. The sample was incubated in a 37° C. incubator for 3 hours and centrifuged at 1400 rpm for 5 minutes. The supernatant was transferred to a flat-bottom 96-well plate, and the UV absorbance at 405 nm (background 700 nm) was measured. As a positive control, distilled water was used, and as a negative control, PBS was used.

Figure 3:
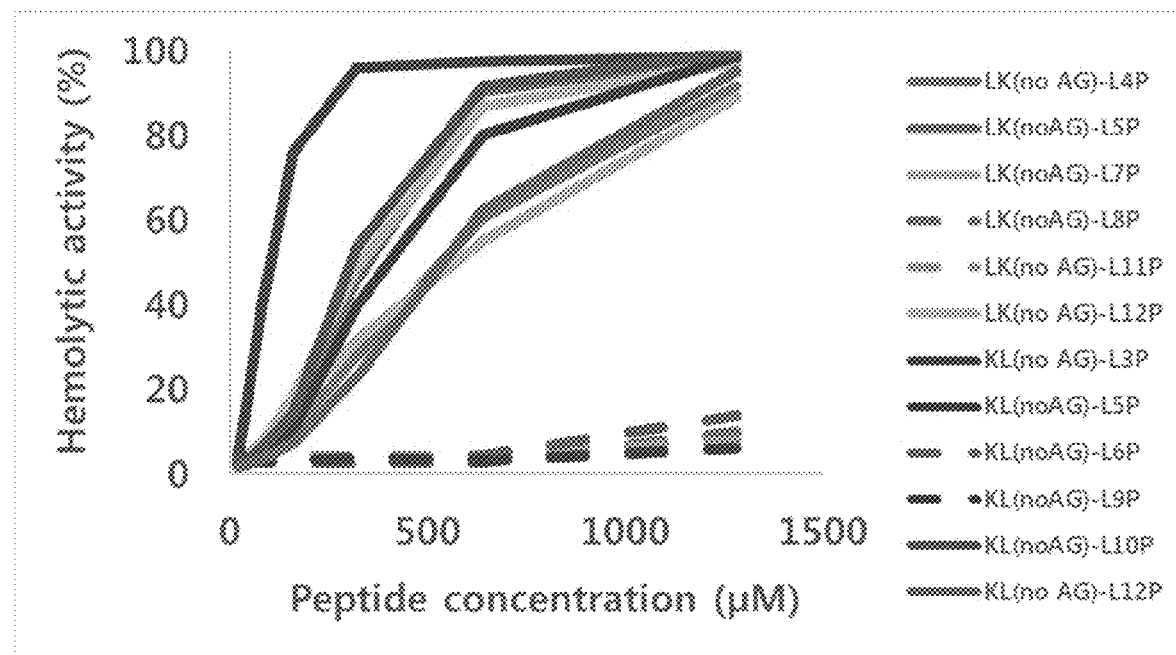
FIG. 3 shows peptides showing the lowest hemolytic activity among LK or KL peptides.

As shown in FIG. 3, the Pro-containing peptides prepared by side-directed mutagenesis could be divided into three classes. The first class includes peptides in which all Lys residues were substituted with Pro. These peptides showed an increased ability to kill Gram-negative bacteria, an increased ability to kill Gram-positive bacteria, and an increased hemolytic activity, and thus did not show specificity for Gram-negative bacteria. Peptides corresponding to the second class were some peptides in which Leu was substituted with Pro, and these peptides showed increased MIC values for E. coli and also relatively high hemolytic activity. The peptides belonging to this class had activity not only against Gram-negative bacteria but also against host cells, and thus were not evaluated to have high specificity for Gram-negative bacteria. Peptides corresponding to the third class were also some peptides in which Leu was substituted with Pro. These peptides showed little or no hemolytic activity and activity against Gram-positive bacteria, while the MIC value thereof for E. coli did not substantially change or slightly decreased compared to that of the peptides in which Leu was not substituted. Although there is a difference in MIC for Gram-negative bacteria, the peptides of this class showed greatly decreased hemolytic activity and a remarkable MIC value for Gram-positive bacteria, and thus were used in the following experiment, with the assumption that these peptides would act specifically against Gram-negative bacteria. In summary, two methods can be used to make a kinked amphipathic alpha-helical structure. The two methods are a method of forming a kinked structure by introducing proline into the hydrophilic side, and a method of forming a kinked structure by introducing proline into the hydrophobic side. Tables 1 and 2 above and FIG. 3 showing hemolytic activity indicate that only a kinked structure formed by introducing proline into the hydrophobic side can change Gram-negative bacteria without causing hemolysis.

Example 3: Conjugation Between Selected Gram-Negative Bacterial Membrane-Specific Peptide and Antibiotic Methotrexate, and Decrease in MIC Value First, whether the three selected peptides would have activity against the Gram-negative bacterial membrane was examined. To this end, the N-terminus of the three peptides was labeled with the fluorescent label TAMRA, and whether the peptides would have activity against the membrane of E. coli was examined. Fortunately, it was observed that the three peptides all entered E. coli at a concentration of about 2.5 to 5 µM (FIG. 4), indicating that all the three peptides can specifically activate the Gram-negative bacterial membrane.

Figure 4:
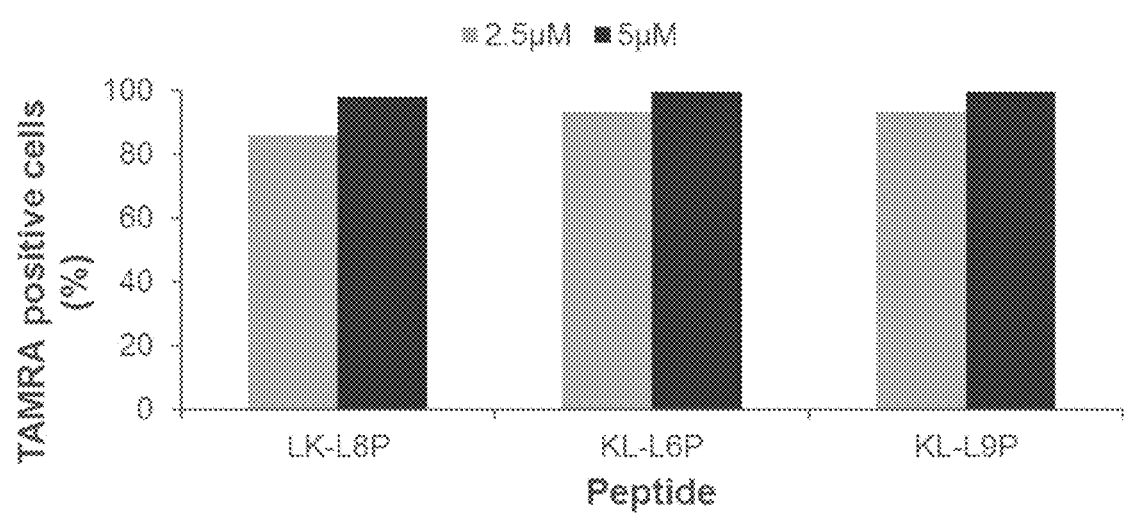
FIG. 4 shows the results of examining whether peptides according to the present invention have the ability to penetrate the membrane of gram-negative bacteria and have activity against the membrane.

The three peptides in FIG. 4 had no hemolytic activity at a concentration of 1 mM in an experiment performed using human red blood cells, and thus it can be expected that when these peptides are used for antimicrobial purposes, they will cause no side effects. However, the peptides have a common feature that the antimicrobial activity thereof against E. coli is not so strong (MIC=10 to 20 µM). In order to decrease this MIC value, MTX (methotrexate), a compound that inhibits folic acid biosynthesis, was conjugated to the N-terminus of each of the peptides, and the MIC values of the three conjugate compounds were measured. As shown in Table 3 below, the MIC values of the three MTX-peptide conjugates were about 2-fold to 4-fold lower than those of the peptides alone. This phenomenon suggests that the peptides selectively act against the E. coli membrane and a portion thereof enters bacteria and effectively kills the bacterial cells. Thus, this method of conjugating the Gram-negative bacterial membrane-specific peptide with an antibiotic that is difficult to enter bacteria may be proposed as a good method for developing a new antibiotic. When many kinds of antibiotics that are difficult to penetrate bacteria are covalently linked to a peptide that causes less side effects and can activate the E. coli membrane to enter the bacterium, they can be used as new antibiotics against Gram-negative bacteria.

TABLE 3

| Peptide | Sequence | MIC [µM] [a] E. coli |
|---|---|---|
| LK-L8P | Ac-LKKLLKLPKKLLKL | 10 |
| Mtx-LK-L8P | Mtx- LKKLLKLPKKLLKL | 5.0 |
| KL-L6P | Ac-KLLKLPKKLLKLLK | 10 |
| Mtx-KL-L6P | Mtx- KLLKLPKKLLKLLK | 5.0 |
| KL-L9P | Ac-KLLKLLKKPLKLLK | 20 |
| Mtx-KL-L9P | Mtx- KLLKLLKKPLKLLK | 5.0 |

[a] MIC (minimum inhibitory concentration): peptide concentration required to the growth of the representative Gram-negative bacterium Escherichia coli (ATCC 25922) by 20%

Example 4: Discovery of New Antibiotic by Membrane-Activating Peptide

Using the three peptides which have minimized hemolytic activity and can activate the Gram-negative bacterial membrane, the following experiment was performed to investigate whether the peptides would be synergistic with colistin. Since colistin has the effect of touching the outer membrane of Gram-negative bacteria, it was inferred that any of the peptides would have *E. coli* membrane-specific activity, as long as it enhances the antimicrobial activity of colistin that touches the outer membrane of *E. coli*. The already selected three peptides (LK-L8P, KL-L6P, KL-L9P) having the property of easily entering Gram-negative bacteria, and four peptides, including LK-L11P, which have good MIC values, were investigated about whether they would be synergistic with colistin. In the experimental method, colistin was simply mixed with each peptide, and *E coli* which is representative of Gram-negative bacteria was treated with the mixture in order to examine whether the ability of the mixture to kill *E. coli* would be enhanced compared to that of the peptide or colistin. In particular, when the ability of colistin to kill Gram-negative bacteria is much enhanced, it can be determined that the peptide has good synergy with colistin (FICI<1.0). "having good synergy" means that two compounds (colistin and the peptide herein) help each other so that they can kill bacteria even at significantly lower concentrations compared to the effects of the two compounds are simply combined (FICI=1.0).

As shown in Table 4 below, synergy with colistin was the highest for the KL-L9P peptide with an FICI (fractional inhibitory concentration index) value of 0.57, and the synergism of the KL-L9P peptide with colistin was significantly better than those of other peptides. The characteristic of the peptide is that it has good synergy with colistin, even though the MIC value of the peptide alone is 5-fold higher than those of other three peptides. It can be inferred that the KL-L9P peptide has a slightly different ability, while the three peptides having good MIC have the property of general antimicrobial peptides that degrades the membrane. The peptide was defined as an *E. coli*-specific membrane-activating peptide, and the following study was performed.

TABLE 4

Synergism of P-mutant peptides having minimized hemolytic activity with colistin

| Peptide alone [a] | MIC (μM) against *E. coli* ATCC 25922 | | Fractional Inhibitory Concentration Index(FICI) [b] Colistin & 1 μM peptide |
|---|---|---|---|
| | | Colistin alone | |
| LK-L8P | 3 | 1.25 | 0.83, Synergism |
| LK-L11P | 3 | | 0.83, Synergism |
| KL-L6P | 3 | | 0.83, Synergism |
| KL-L9P | 15 | | 0.57, Synergism |

[a] LK sequence: Ac-LKKLLKLLKKLLKL-NH$_2$, and KL sequence: Ac-KLLKLLKKLLKLLK-NH$_2$.
[b] The FICI value is identified as inhibitory concentration, bacterial growth of the control <10% FICI = MIC$_{A+B}$/MIC$_A$ + MIC$_{B+A}$/MIC$_B$. Synergism is defined as FICI ≤1, additivity to independence is defined as FICI = 1-4.

Example 5: Membrane Activating Mechanism of Selected KL-L9P Peptide

Next, a mechanism how the selected KL-L9P peptide activates the membrane was investigated. Penetration into the microbial outer membrane was measured by the fluorescence intensity of NPN-treated *E. coli* (λex=355 nm, λem=405 nm). An *E. coli* suspension (8×10$^7$ cells/mL) was centrifuged at 13000 rpm at 25° C. for 10 minutes, and suspended in 5 mM HEPES buffer (pH 7.2). NPN was added to the *E. coli* suspension to a final NPN concentration of 5 μM. The fluorescence intensity of the *E. coli* suspension was measured using the FL-55 fluorometer. The peptide together with 5 μM NPN was added to the *E. coli* suspension. Fluorescence intensity (F.I.)=F.I. of peptide added to *E. coli* suspension—F.I. of *E. coli* suspension containing 5 μM NPN.

Figure 5:
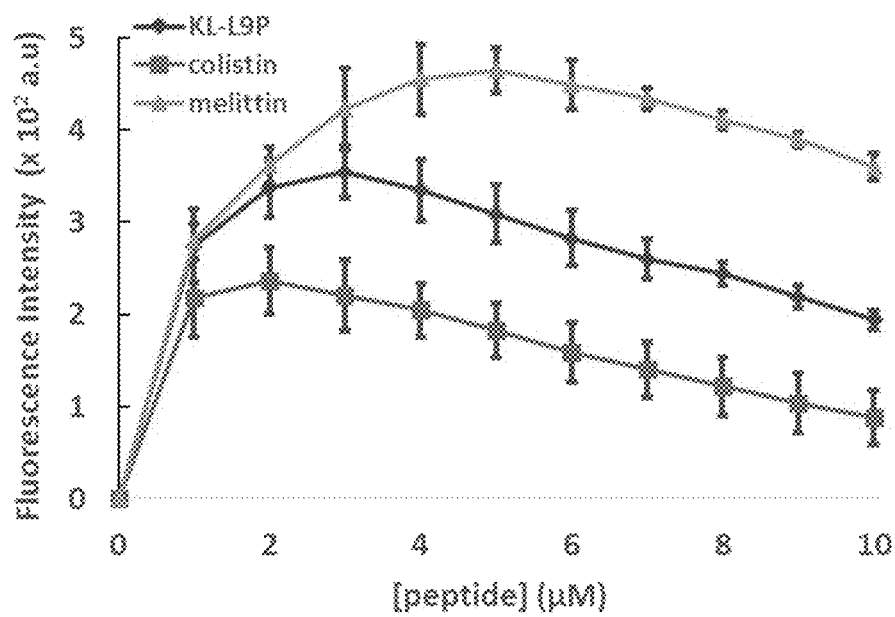
FIG. 5 shows the results of observing fluorescence using naphthylphenylamine (NPN) in the presence of E. coli in order to confirm the mechanism by which a peptide according to the present invention activates the membrane.

First, fluorescence using NPN (naphthylphenylamine) was observed in the presence of *E. coli*, and as a result, it was shown that KL-L9P and colistin had the property of touching the outer membrane and entering the outer membrane (FIG. 5). It was measured using KL-L9P and the competitive drug colistin, and as a result, it could be seen that KL-L9P had a better effect of loosening the outer membrane than colistin when compared in unit moles. Melittin known to perforate the membrane also had a high ability to increase NPN fluorescence. However, it is inferred that the KL-L9P peptide cannot perforate the membrane due to its short length.

In the second experiment, whether the peptides would have the ability to disrupt both the outer wall and inner wall of bacteria was examined. To this end, the fluorescent dye Sytox Green capable of specifically staining DNA was used, and penetrability into the microbial membrane was evaluated from the average fluorescence intensity of *E. coli* treated with SYTOX Green. An *E. coli* suspension (2×10$^8$ cells/mL) was incubated with the three peptides in the presence of SYTOX Green (2.5 μM) for 10 minutes, respectively. Penetrability was quantified by a (fluorescence activated cell sorter (FACS). The average fluorescence intensity of 1×10$^4$ gate cells was measured. Melittin (control) is a pore-forming peptide that disrupts the microbial cell membrane.

Figure 6:
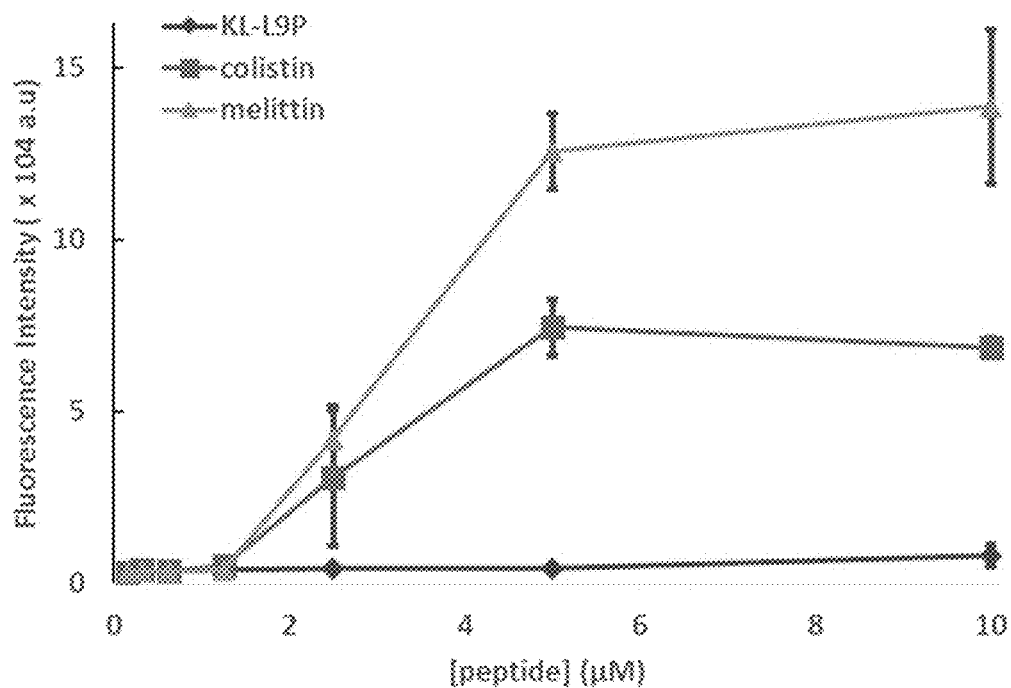
FIG. 6 shows the results of observing whether a peptide according to the present invention degrades or disrupts the outer wall or inner wall of Gram-negative bacteria.

It was determined that KL-L9P did not stain DNA, whereas colistin easily stained DNA. This indicates that the KL-L9P peptide has no ability to degrade or penetrate the inner wall, whereas colistin and pore-forming melittin have this ability (FIG. 6).

An LPS extract (Sigma) and the peptide were suspended in PBS buffer. At 25° C., each sample containing 0.5 mg/mL LPS alone or 0.5 mg/mL LPS and 500 μM peptide was measured in three sets. The volume size value with the greatest volume percentage was selected, and the volume size diameter (nm) was calculated.

Figure 7:
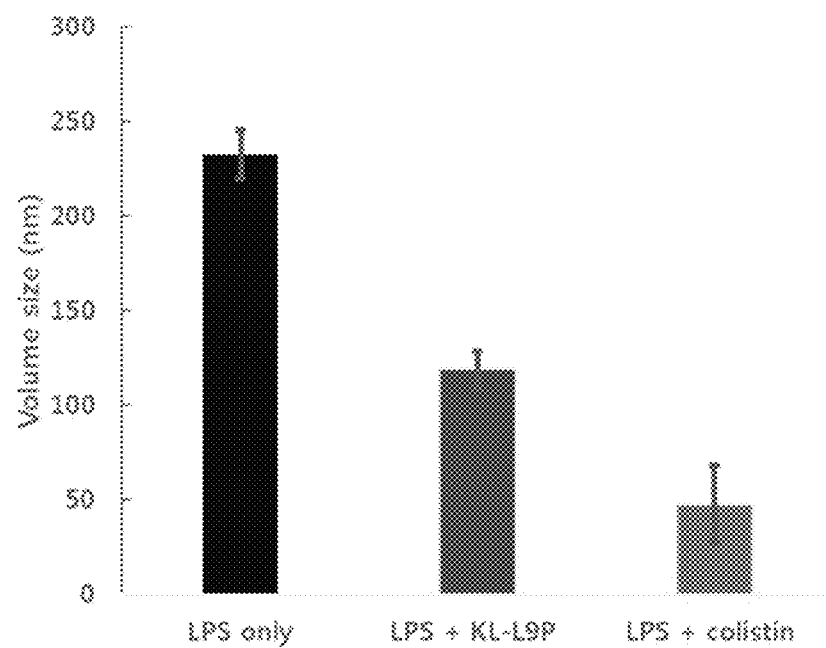
FIG. 7 shows the results of measuring a change in the size of a liposome composed of LPS or the size of the liposome in the presence of a peptide by DLS.

The stability of liposomes composed of LPS was examined in the presence of KL-L9P and colistin, and as a result, it could be seen that colistin has the property of dividing liposomes finely, whereas KL-L9P had this property, but the degree of this property of KL-L9P was not serious (FIG. 7).

*E. coli* NDm-1 was diluted when it reached OD$_{600}$=0.5. The microorganism was treated with 2.5 μM of the peptide in a 37° C. incubator for 30 minutes. LK-L12P was used as a positive control. The peptide strongly induced leakage from the inner membrane and the outer membrane. A confocal image of KL-L9P indicated that TAMRA-labeled KL-L9P was distributed around the thin peri-cytoplasmic membrane, unlike LK-L12P.

Figure 8:
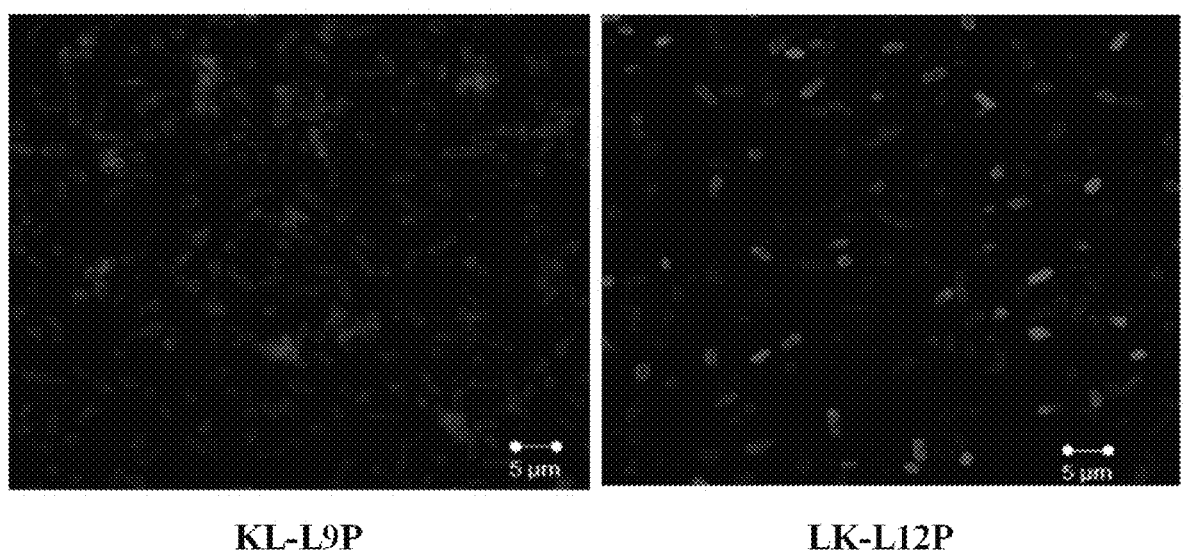
FIG. 8 shows confocal microscopic images for NDm-1 staining of E. coli treated with a TAMRA-conjugated peptide.

In fact, when the presence of the fluorescence-labeled KL-L9P peptide in *E. coli* was observed with a confocal microscope, it can be seen that ring-shaped fluorescent L9P molecules are distributed in almost all *E. coli* cells. This phenomenon is clearly distinguished from a phenomenon in which the LK-L12P having a slightly better MIC value and the ability to degrade the membrane stains all microbial cells or in which a larger portion of microbial cells are labeled by the fluorescence-labeled peptide (FIG. 8).

From the results of the above-described four experiments, it could be seen that the KL-L9P peptide has an excellent ability to penetrate the outer membrane of Gram-negative bacteria, compared to other peptides, while it has no ability to break the membrane and remains in the penetrated state. Thus, the KL-L9P peptide can loosen the membrane so that small hydrophobic molecules that could not enter can enter the membrane.

Example 6: Synergy of KL-L9P with Repositioned Drug

An experiment was performed to demonstrate whether the antimicrobial activity of other compounds against Gram-negative bacteria would be improved in the presence of the KL-L9P peptide. To this end, two antibiotics, linezolid and cloxacillin, were selected. The two compounds have a common feature that they are antibiotics that are used only against Gram-positive bacteria, and particularly, lack the ability to pass through the outer membrane of Gram-negative bacteria, and thus have little or no efficacy against Gram-negative bacteria. If KL-L9P has synergism with the two compounds (linezolid and cloxacillin) with respect to antimicrobial activity against E. coli, it is expected that the Gram-negative bacteria-specific membrane-activating peptide wanted by the present inventors helps the intracellular penetration of the two compounds (linezolid and cloxacillin).

Figure 9:
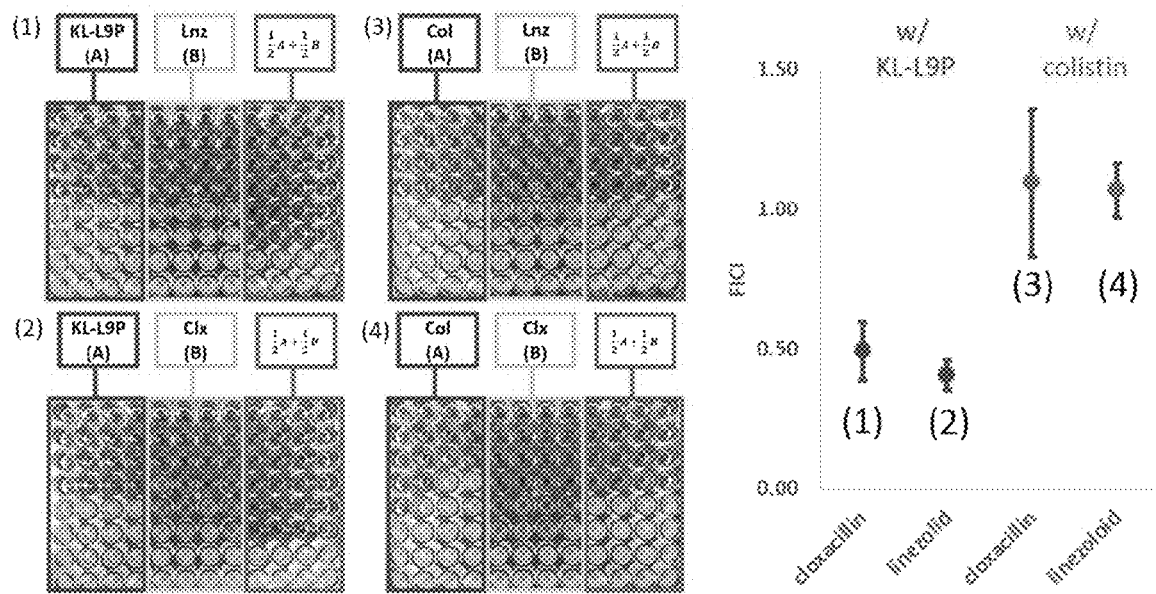
FIG. 9 shows the results of evaluating the synergistic effect of KL-L9P and linezolid or cloxacillin.

KL-L9P had synergism with linezolid or cloxacillin and greatly enhanced the ability of linezolid or cloxacillin to kill Gram-negative bacteria. In addition, whether the competitive drug colistin would be synergistic with the two drugs was observed, and as a result, it could be seen that colistin had little or no synergism with the two drugs (FIG. 9). Synergism of the membrane-activating peptide KL-L9P with linezolid or cloxacillin. (1) and (2) treated with the membrane-activating peptide KL-L9P and linezolid or cloxacillin showed an FICI value of less than 0.5, indicating that the peptide has synergy with the drug. (3) and (4) treated with colistin and linezolid or cloxacillin showed an FICI value of about 1, indicating that the peptide has no synergy with the drug.

Figure 10:
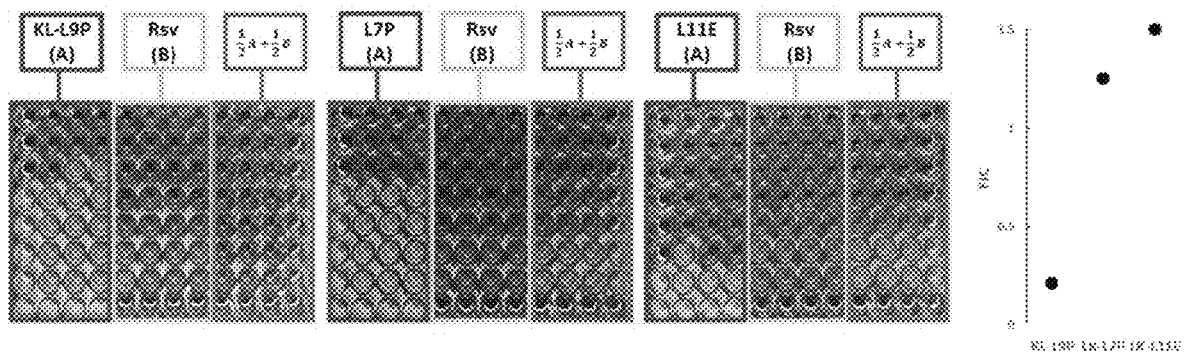
FIG. 10 shows the results of evaluating the synergistic effect of KL-L9P and resveratrol.

If so, in order to investigate whether other similar peptides have no synergy with compounds known to have antimicrobial activity, examination was performed to determine whether LK-L7P and LK-L11E having the highest antimicrobial activity against E. coli would have synergy with resveratrol known to have weak antimicrobial activity. As shown in FIG. 10, KL-L9P that remains in the membrane had good synergy, whereas the other two peptides had no synergy despite their strong antimicrobial activity. Regarding the synergy of membrane-activating peptide KL-L9P with resveratrol, the membrane-activating peptide KL-L9P had strong synergy with resveratrol (FICI=0.2), whereas LK-L7P or LK-L11E, the MIC value of which against E. coli is at least 5-fold lower (better) that that of the membrane-activating peptide KL-L9P, had no synergy (FICI=1 or more).

As a result, the two experiments as described above demonstrated that KL-L9P specifically activates the membrane of E. coli, and shows great synergy.

Next, an experiment was performed to investigate whether KL-L9P would have synergy with non-antibiotics other than antibiotics. In order to examine synergy, among NSAID drugs which have been most frequently used, the following drugs were selected: aspirin, ibuprofen, acetaminophen and the like; atorvastatin which hyperlipidemia therapeutic agents that keep the number one spot in sales, lovastatin and simvastatin. In addition, various natural materials such as curcumin, berberine and the like were selected, which are known to have medicinal effects but pose problems in terms of water solubility and efficacy. Since it was already reported that compounds are about to examine synergy with KL-L9P could have somewhat medicinal effects against Gram-negative bacteria, the antimicrobial activity of these compounds is somewhat known. However, since it has not been reported that co-administration of these compounds with the Gram-negative bacterial membrane-activating peptide can kill Gram-negative bacteria even at low concentrations, an experiment was performed to examine whether these drugs would have great synergistic effects, in order to determine whether these drugs would be used as antibiotics.

Figure 17:
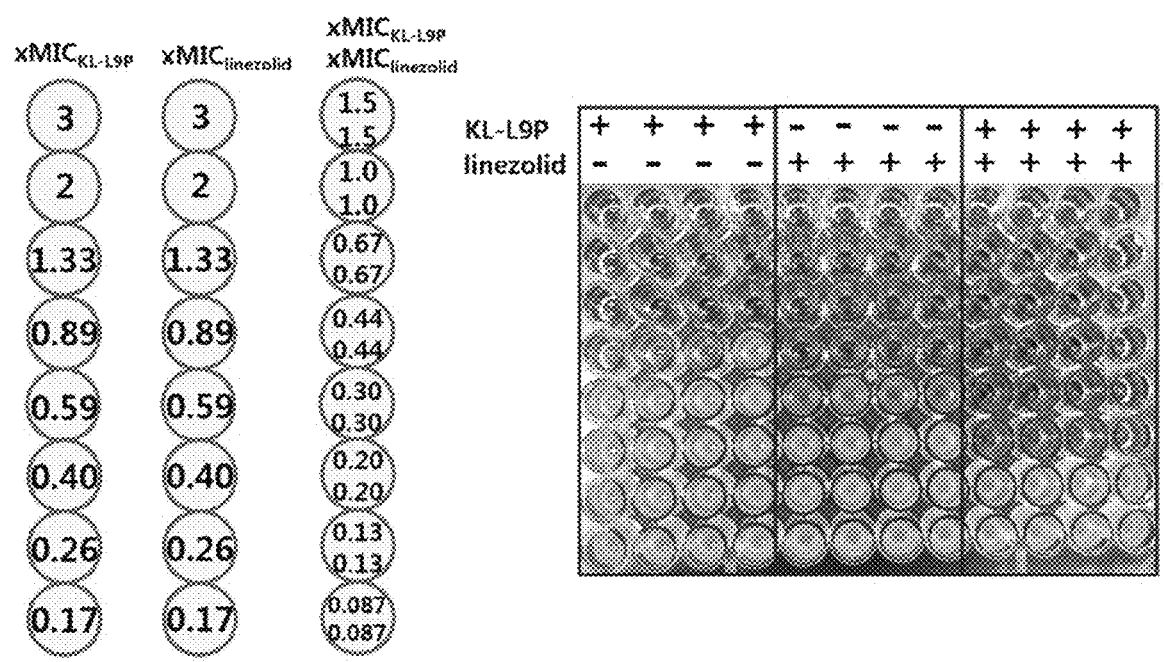
FIG. 17 shows the method of Wimley for evaluating synergistic effects (BBA, 2015, v. 1848(1), pp. 8-15.).

Synergy was evaluated by an antibiotic interaction assay (Wimley, 2015) Using the method of Wimley (BBA, 2015, v. 1848(1), pp. 8-15), synergy between the membrane-activating peptide and an antibiotic was measured by an FICI value (FIG. 17). MIC assay shows about 2 to 4 folds difference depending on experimental conditions. Thus, to accurately examine synergy, a ⅔ dilution method which observes MIC at denser concentration intervals is advantageous over a ½ dilution method in statistical terms. Namely, starting with the concentration of the membrane-activating peptide (first line) which corresponds to 3×MIC, ⅔ dilution is performed, and the MIC of the peptide is measured. In the same manner, the MIC of an antibiotic or repositioning drug (second line) is measured. In the third line, the two compounds are mixed after putting half amount each, and the MIC thereof is measured. As can be seen in FIG. 7, when the mixture of the two compounds can easily kill Gram-negative bacteria at lower concentrations compared to each compound alone, it can be considered having high synergy.

A broth microdilution technique (⅔ dilution) was used together with an MH broth. E. coli treated with an antibiotic and the peptide was incubated in a 37° C. incubator for 18 hours.

The results of the experiment indicated that many drugs corresponding to 69% had good synergy with KL-L9P (FICI<0.5), and could kill E. coli at lower concentrations than concentrations at which they were used alone to kill E. coli (Table 5). For example, cloxacillin had an MIC value of 0.3 μM (128-fold diluted), and linezolid had an MIC value of 10 μM (about 16-fold diluted). Among NSAIDs, ibuprofen had an MIC value of 3 μM (about 3000-fold diluted), and curcumin had an MIC value of 4 μM (about 330-fold diluted). These compounds all could exhibit synergy with 1 μM of the Gram-negative bacterial membrane-activating peptide KL-L9P.

TABLE 5

Synergy of antibiotic and non-antibiotic drugs and natural drugs with KL-L9P
E. coli ATCC 25922

| antibiotic | MIC[a] of antibiotic (μM) | MIC of KL-L9P (μM) | MIC of combination (μM) | | $FICI_{antibiotic}$ | $FICI_{KL-L9P}$ | FICI[b] |
|---|---|---|---|---|---|---|---|
| | | | antibiotic | KL-L9P | | | |
| colistin | 1.63 | 14.82 | 0.17 | 2.40 | 0.10 | 0.16 | 0.26 |
| cloxacillin | 74.08 | 11.85 | 17.78 | 2.96 | 0.24 | 0.25 | 0.49 |
| linezolid | 71.11 | 14.85 | 15.80 | 2.60 | 0.22 | 0.18 | 0.40 |
| resveratrol | 1770.84 | 14.17 | 246.91 | 1.59 | 0.14 | 0.11 | 0.25 |
| berberine | 298.35 | 13.61 | 273.15 | 7.22 | 0.92 | 0.53 | 1.45 |
| curcumin | 395.83 | 19.50 | 78.70 | 1.89 | 0.20 | 0.10 | 0.30 |
| (S)-ibuprofen | 12000.00 | 10.00 | 416.67 | 2.00 | 0.03 | 0.20 | 0.23 |
| (R)-ibuprofen | 12000.00 | 12.00 | 555.56 | 2.70 | 0.05 | 0.23 | 0.27 |
| aspirin | 518.52 | 19.50 | 479.17 | 12.95 | 0.92 | 0.66 | 1.59 |
| quercetin | 7500.00 | 15.00 | 108.39 | 5.00 | 0.01 | 0.33 | 0.35 |
| simvastatin | >500 | 11.50 | 52.47 | 1.27 | 0.07 | 0.11 | 0.18 |
| lovastatin | >500 | 13.00 | 74.07 | 1.78 | 0.10 | 0.14 | 0.24 |
| atorvastatin | >500 | 10.50 | 166.67 | 4.00 | 0.22 | 0.38 | 0.60 |

[a]Minimal inhibitory concentration was determined by <20% growth percent of positive control.
[b]The FICI (fractional inhibitory concentration index) = $MIC_{A+B}/MIC_A + MIC_{B+A}/MIC_B$. FICI ≤ 0.5 for synergy. 0.5 < FICI ≤ 1 for additivity to independence, 1 < FICI ≤ 2 for antagonism, 2 ≤ FIC < 4 for inhibition.

Example 7: Synergy of KL-L9P/Colistin with Repositioning Drug

Although colistin did not show great synergy when co-administered with a conventional antibiotic or a repositioning drug newly identified as an antibiotic (compared to KL-L9P), the membrane-activating peptide invented in the present invention and MOA (Mode of Action) could activate the membrane in a different manner. Since colistin is still used as a golden standard reagent that loosens the membrane, it may be used as an outer membrane-specific activating peptide. In addition, since the present inventors already found that there is high synergy between colistin and KL-L9P, an experiment was performed to examine how linezolid and curcumin, which showed synergy with KL-K9P, would show synergy when the two membrane-activating peptides were present at the same time. To this end, in the present invention, the synergy of a repositioning drug in the presence of both the membrane-activating peptide KL-L9P and colistin was examined. The three compounds were mixed with one another and co-administered for eradiation of Gram-negative bacteria. In this regard, the two compounds were the membrane-activating peptide KL-L9P and colistin, and the remaining one was a conventional drug or a repositioning drug.

To measure the synergy between the membrane-activating peptides and the repositioning drug, a 10× compound was prepared, and then serially diluted ⅔-fold with distilled water. An MH broth (900 μl) was added to and mixed with the 10× compound (100 μl), and then 200 μL of the mixture was taken and added to a 96-well plate. E. coli cultured for one day was adjusted to 0.5 MCF using McFarland, and diluted 10-fold, and then 10 μl of the dilution was added to each well of the plate (5×10⁵ CFU/mL). After addition of the bacterial cells, plate was incubated at 37° C. for 18 hours, and then the OD value at UV-Vis (600 nm) was measured. Cell viability (%)=(OD₆₀₀ of sample–OD₆₀₀ of negative control)/(OD₆₀₀ of positive control–OD₆₀₀ of negative control)×100. MIC was determined based on the concentration corresponding to cell viability<20%.

The synergy of the three compounds was comparable to the best of the three synergies obtained for the two compounds. This is a very good result. This is because, when the synergy (FICI) value of the mixture of the two compounds is 0.3, the mixture kills E. coli at about 7-fold diluted concentrations compared to when the two compounds are used alone, whereas, when co-administration of the three compounds shows an FICI value of 0.3, it kills bacteria at 10-fold diluted concentrations compared to when the three compounds are used alone. In the present invention, the synergy value (FICI) of KL-L9P/colistin/linezolid was found to be 0.28. When the three compounds were used alone, they showed MICs of 13 uM, 0.8 uM and 60 uM, respectively, and when they were used in combination, they could kill E. coli at concentrations of 1 uM, 50 nM and 6 uM, respectively, which were 12-fold, 16-fold and 10-fold lower, respectively. Such results can reach the provisional conclusion that the synergy when the three compounds are co-administered can be greater than the synergy between the two compounds. If anticipated in this way, the synergy of antibiotics (n in number) is unimaginably great. Thus, it can be expected that when various compounds are mixed with one another in nature, amplified antimicrobial activity by the great synergy of the compounds will appear. This expectation is also possible only when one or more of the compounds are membrane-activating peptides.

In addition, among the three synergies obtained for the two-compound pairs, the highest synergy was obtained by the use of KL-L9P. This suggests that the KL-L9P peptide discovered by the present inventors has the greatest effect on the synergy and the synergy is dependent on the KL-L9P peptide. However, the present inventors would like to pay attention to the synergistic effect of colistin. This is because if colistin can show synergy with conventional drugs used for other purposes so as to kill Gram-negative bacteria, the two drugs for co-administration can immediately be used as drugs unless they have toxicity, even though colistin shows lower synergy than KL-L9P. Namely, since the two drugs are commercially used, drug repositioning in a true sense is possible. Synergy against Gram-negative bacteria is usually expressed as FICI (fractional inhibitory concentration index). When the FICI value is 0.5 or less, it is considered synergistic, and when the FICI value reaches about 0.2, it is considered that MIC can be at least 10-fold reduced compared to MIC obtained when two antibiotics are used alone. In the present invention, many kinds of compounds reaching a synergy of 0.2 to 0.4 with colistin were found. These compounds include curcumin, two isomers of ibuprofen, simvastatin, and the like.

Example 8: Examination of General Properties of Membrane-Activating Peptide

A) General Conditions of Membrane-Activating Peptide

KL-L9P has greater synergy than other mutant peptides, and the general properties of this compound need to be examined. First, the alpha-helical content of the peptide is higher under membrane conditions than under 100% water conditions. Although the peptide deviates from the exact helical shape of an exact cylindrical shape by Pro, it is certain that the separated shape between the hydrophilic side and the hydrophobic side of the helical makes membrane activity strong. The structure of KL-L9P predicted by the PyMol program also shows a kinked alpha helix. It is generally believed that the Pro-mutant portion forms a vertex at which the alpha helix is kinked, but the shape predicted by PyMol indicates that the kinked portion is the boundary between the hydrophilic side and the hydrophobic side. It is believed that the exact shape of this portion can be determined only after studies on the detailed shape were conducted, but the fact that the retention time of the peptide in the membrane can be increased by the kinked shape can be seen through various chemical experiments. In this case, mutant peptides capable of forming excessively long alpha helices were already excluded in first screening. In the conditions of first screening, a peptide having the lowest hemolytic activity against host cells was selected, and in this case, it is believed that mutant peptides capable of forming excessively long alpha helices were already completely excluded.

It is believed that when the peptide having a short alpha helix length and a high alpha helix content remains in the membrane for a long time, ion-clustering may occur with respect to the peptide in the outer membrane of Gram-negative bacteria. In this case, the membrane itself can become loose while the flow of molecules in the membrane increases. When the membrane becomes loose, many low-molecular antibiotic candidates that could not pass the non-loosened membrane can now pass through the membrane and enter the membrane, and thus exhibit antimicrobial effects while showing synergy with the peptide.

Since the Pro amino acid added to the hydrophobic side shows hydrophobicity, it does not interfere with the recognition of long hydrocarbon chains in the membrane by the peptide. It appears that the separation between kinked hydrophilic and hydrophobic sides allows to recognize the cations of the hydrophilic side and the anions on the membrane surface at both termini (N-terminus and C-terminus). This is because, if a completely cylindrical alpha-helix is formed, the recognition of the molecule of the membrane by the hydrophilic side is made strong, the recognition by the hydrophobic side will be weakened, and when the recognition of the molecule of the membrane by the hydrophobic side is made strong, the recognition by the hydrophilic moiety can be weakened. A long alpha-helical shape increases the potential to degrade the membrane of eukaryotic cells by hemolytic activity against host cells.

The difference of KL-L9P from isomers in which proline is introduced into other positions is that this peptide is very hydrophilic so that it can have the shortest retention time under the same HPLC condition. This is believed to be because positive charging in KL-L9P is concentrated on one side. In this case, the peptide may have clearer amphipathicity. The fact that the membrane-activating peptide generally has the shortest retention time also corresponds to LK-L7PL8P and LK-L8D, which have the best synergy among compounds in which two proline residues are introduced.

B) Synthesis of Peptide Substituted with Two Pro Residues and Synergy Thereof

If so, an experiment was performed to examine whether only KL-L9P among all possible mutants of LK or KL would activate the outer membrane of Gram-negative bacteria. First, the Pro-mutation in the LK peptides and the KL-peptides was increased from one to two. This is because the Pro-mutation can show a kinked structure, and thus when two Pro residues rather than one are added to the peptide, the peptide may have a more kinked shape. Peptides in which two positions among several possible positions were mutated with Pro were prepared, and these peptides are shown in Table 6 below.

TABLE 6

Amino acid sequences of LK 2 Pro mutants, MIC values against Escherichia coli (ATCC 25922) and Staphylococcus aureus (ATCC 29213), and MHC values for hemolysis

| Peptide | Sequence | MIC [μM] [a] Against E. coli | MIC [μM] Against S. aureus | MHC [μM] [b] |
|---|---|---|---|---|
| LK | LKKLLKLLKKLLKL (SEQ ID NO: 5) | 20 | 20 | 0.3 |
| LK-L4PL5P | LKKPPKLLKKLLKL (SEQ ID NO: 41) | 5 | >40 | >1280 |
| LK-L4PL8P | LKKPLKLPKKLLKL (SEQ ID NO: 42) | 40 | >40 | >1280 |
| LK-L4PL11P | LKKPLKLLKKPLKL (SEQ ID NO: 43) | >40 | >40 | >1280 |
| LK-L5PL8P | LKKLPKLPKKLLKL (SEQ ID NO: 44) | 20 | >40 | >1280 |
| LK-L5PL11P | LKKLPKLLKKPLKL (SEQ ID NO: 45) | 40 | >40 | >1280 |
| LK-L7P8P | LKKLLKPPKKLLKL (SEQ ID NO: 46) | 40 | >40 | >1280 |
| LK-L7PL11P | LKKLLKPLKKPLKL (SEQ ID NO: 47) | 20 | >40 | >1280 |
| LK-L8PL11P | LKKLLKLPKKPLKL (SEQ ID NO: 48) | 40 | >40 | >1280 |
| LK-L11PL12P | LKKLLKLLKKPPKL (SEQ ID NO: 49) | 2.5 | >40 | >1280 |

[a] MIC (minimum inhibitory concentration): peptide concentration to inhibit growth of the representative Gram-negative bacterium Escherichia coli (ATCC 25922) by 20%
[b] MHC (minimum hemolytic concentration): peptide concentration required to cause 10% hemolysis in hRBCs In screening for peptides introduced with two Pro residues, whether the peptide would have synergy with colistin was also examined. These peptides introduced with two Pro residues are characterized in that the MIC values of these peptides (except for LK-L4PL5P and LK-L11PL12P) against Gram-negative bacteria are significantly higher than that of the peptides introduced with one Pro, and thus need to be used at several tens μM or higher to kill Gram-negative bacteria. This means that the ability of the peptide to penetrate or degrade the membrane is significantly reduced, and in this case, the toxicity of the peptide against host cells can significantly decrease, indicating that the peptide is a good new peptide drug. The LK-L11PL12P peptide showing a low MIC of 2.5 uM against *E. coli* may be used alone as a new drug. Among several peptides introduced with two Pro residues, the LK-L7PL8P mutant peptide showed the best synergy with colistin. The FICI of this mutant with colistin reaches 0.3, suggesting that this peptide is almost comparable to KL-L9P. However, this peptide has a disadvantage in that because it has synergy with colistin at a concentration of about 8.4 µM, it should be used in 4 to 5-fold larger amounts, while KL-K9P has the greatest synergy with colistin at a concentration of 2.6 µM. LK-L7P/L8P also had synergy with linezolid (FICI: about 0.53). This peptide had partial synergy which was slightly lower than the FICI value of KL-L9P (0.40) (Table 7). The LK-L7PL8P peptide showed an FICI value of 0.27, which was similar to that of LK-L9P, when it was mixed with colistin and linezolid. Thus, the synergy of this peptide may not be so small (Table 8). The shape of the LK-L7P/L8P peptide predicted by a peptide shape prediction program, has a shape in which two alpha helices are broken by the Pro portion. Thus, this shape can be the general characteristic of the peptide that gives synergy.

C) Fabrication of D-Form Peptide Using D-Amino Acids

A KL-L9P-D peptide was prepared by substituting all the amino acids of the KL-L9P peptide with D-amino acids, and the synergy of the prepared peptide with colistin and linezolid was examined. The reason why the KL-L9P-D peptide was prepared is because it is believed that the chemical stability thereof and the stability thereof against the natural enzyme protease can be better than a peptide consisting of naturally occurring L-amino acid, and the recognition of the membrane by the peptide cannot be influenced by the chiral structure, and thus the D-form peptide may have synergy comparable to that of the L-form peptide. However, it could be seen that the synergy of the D-form was not significantly greater than that of the L-form. Colistin showed partial synergy of FICI=0.38, and linezolid showed partial synergy of FICI=0.66. This reached the conclusion that the recognition portion of the peptide can recognize a portion of the membrane which is not associated with the chiral portion a lot, and it recognizes also a portion of the membrane which is associated with the chiral portion (for example, phosphate anions, etc.). However, in view of the fact that the D form has overall synergy, it mainly recognizes a non-chiral portion present in the membrane, and for this reason, it may be used as a peptide that can exhibiting a synergistic effect on killing Gram-negative bacteria.

TABLE 7

Synergy of LK-L7PL8P with colistin and linezolid
*E. coli* ATCC 25922

| Peptide | MIC[a] of colistin (µM) | MIC of peptide (µM) | MIC of combination (µM) | | $FICI_{colistin}$ | $FICI_{Peptide}$ | FICI[b] |
|---|---|---|---|---|---|---|---|
| | | | antibiotic | peptide | | | |
| LK-L7PL8P | 0.50 | 53 | 0.09 | 8.4 | 0.18 | 0.16 | 0.34 |

| Peptide | MIC[a] of Linezolid (µM) | MIC of peptide (µM) | MIC of combination (µM) | | $FICI_{linezolid}$ | $FICI_{Peptide}$ | FICI[b] |
|---|---|---|---|---|---|---|---|
| | | | linezolid | peptide | | | |
| LK-L7PL8P | 83 | 53 | 22 | 14 | 0.27 | 0.26 | 0.53 |

Synergy effect was evaluated by the novel antibiotic interaction assay (Wimley, 2015). Broth microdilution technique (2/3 0dilution) was used with MH Broth. Antibiotic, peptide treated *E. coli* was incubated 18 hours at 37° C. incubator.
[a]Minimal inhibitory concentration was determined by <20% growth percent of positive control.
[b]The FICI (Fractional inhibitory concentration index) = $MIC_{A+B}/MIC_A$ + $MIC_{B+A}/MIC_B$. FICI < 0.5 for synergy, 0.5 ≤ FICI < 1 for partial synergy, 1 ≤ FICI ≤ 2 for additivity to independence, and FIC > 2 for antagonism.

TABLE 8

Synergy of LK-L7PL8P with colistin and linezolid
*E. coli* ATCC 25922

| Peptide | MIC[a] of combination (µM) | | | $FICI_{colistin}$ | $FICI_{linezolid}$ | $FICI_{Peptide}$ | FICI[b] |
|---|---|---|---|---|---|---|---|
| | colistin | linezolid | peptide | | | | |
| LK-L7PL8P | 0.040 | 5.9 | 4.7 | 0.09 | 0.11 | 0.07 | 0.27 |

Synergy effect was evaluated by the novel antibiotic interaction assay (Wimley, 2015). Broth microdilution technique (2/3 dilution) was used with MH Broth. Antibiotic, peptide treated *E. coli* was incubated 18 hours at 37° C. incubator.
[a]Minimal inhibitory concentration was determined by <20% growth percent of positive control.
[b]The FICI (Fractional inhibitory concentration index) = $MIC_{A+B}/MIC_A$ + $MIC_{B+A}/MIC_B$. FICI < 0.5 for synergy, 0.5 ≤ FICI < 1 for partial synergy, 1 ≤ FICI ≤ 2 for additivity to independence, and FIC > 2 for antagonism.

D) Creation of Kinked Structure by Mutation Using Amino Acids Other than Pro When hydrophilic amino acids other than Pro are added to the hydrophobic side of an amphipathic peptide, the overall amphipathicity of the alpha helices can be broken, and a bent shape can be partially obtained. Due to a decrease in the alpha-helical content together with this breakage of amphipathicity, the side effects of the peptide on host cells can be reduced, and thus the addition of these amino acids may have the same effects as those of the addition of Pro. Accordingly, mutant peptides were prepared by adding other hydrophilic amino acids (G, S, N, Q, D and E) instead of Pro in KL-L9P having synergy, and the synergies of these mutant peptides were examined.

TABLE 9

| Peptide | Sequence | MIC [μM] [a] Against E. coli |
|---|---|---|
| KL L9G | KLLKLLKKGLKLLK (SEQ ID NO: 26) | 1.25 |

TABLE 9-continued

| Peptide | Sequence | MIC [μM] [a] Against E. coli |
|---|---|---|
| KL L9S | KLLKLLKKSLKLLK (SEQ ID NO: 27) | 1.25 |
| KL L9N | KLLKLLKKNLKLLK (SEQ ID NO: 28) | 2.5 |
| KL L9Q | KLLKLLKKQLKLLK (SEQ ID NO: 29) | 1.25 |
| KL L9D | KLLKLLKKDLKLLK (SEQ ID NO: 30) | 20 |
| KL L9E | KLLKLLKKELKLLK (SEQ ID NO: 31) | 5 |

[a] MIC (minimum inhibitory concentration): peptide concentration required to inhibit growth of the representative Gram-negative bacterium *Escherichia coli* (ATCC 25922) by 20%.

TABLE 10

| | (nM) | | | | | | | |
|---|---|---|---|---|---|---|---|---|
| | 400.00 | 266.67 | 177.78 | 118.52 | 79.01 | 52.67 | 35.12 | 0 |
| colistin | 1% | 83% | 94% | 96% | 95% | 95% | 92% | 93% |
| KL L9G 600 nM | 0% | −1% | 39% | 89% | 92% | 87% | 87% | 90% |
| KL L9S 600 nM | 0% | 0% | 21% | 81% | 87% | 86% | 84% | 87% |
| KL L9N 600 nM | −1% | 36% | 39% | 85% | 89% | 88% | 88% | 89% |
| KL L9Q 600 nM | 1% | 0% | 39% | 80% | 86% | 86% | 87% | 88% |
| KL L9D 5 uM | 0% | 0% | 0% | 2% | 48% | 52% | 61% | 79% |
| KL L9E 1.25 uM | 1% | 0% | 3% | 83% | 88% | 87% | 87% | 87% |
| KL L9P 5 uM | 0% | 0% | 0% | 0% | 84% | 77% | 88% | 83% |

TABLE 11

| | (uM) | | | | | | | |
|---|---|---|---|---|---|---|---|---|
| | 250 | 166.67 | 111.11 | 74.07 | 79.01 | 32.92 | 21.94 | 0 |
| simvastatin | 67% | 67% | 71% | 77% | 87% | 93% | 88% | 106% |
| KL L9G 600 nM | 55% | 64% | 63% | 68% | 61% | 75% | 75% | 98% |
| KL L9S 600 nM | 62% | 61% | 74% | 59% | 64% | 76% | 78% | 88% |
| KL L9N 600 nM | 73% | 69% | 63% | 68% | 66% | 78% | 81% | 96% |
| KL L9Q 600 nM | 72% | 69% | 59% | 64% | 72% | 83% | 87% | 96% |
| KL L9D 5 uM | 15% | 4% | 2% | 1% | 37% | 64% | 69% | 66% |
| KL L9E 1.25 uM | 43% | 48% | 79% | 15% | 64% | 77% | 88% | 90% |
| KL L9P 5 uM | 15% | 5% | 2% | 1% | 1% | 39% | 74% | 71% |

Through a simple experiment, it could be seen that only L9D together with L9P had synergy. Using the method of Wimley, the synergies of the peptide with colistin and simvastatin were measured by FICI values. As shown in Table below, the FICI values of KL-L9D with colistin and simvastatin were 0.46 and 0.61, respectively, indicating that the effects of KL-L9D were significantly lower than those of the KL-L9P peptide showing FICI values of 0.26 and 0.18.

TABLE 12

Synergies of KL-L9D with colistin and simvastatin
*E. coli* ATCC 25922

| Peptide | MIC[a] of colistin (μM) | MIC of peptide (μM) | MIC of combination (μM) | | FICI$_{antibiotic}$ | FICI$_{Peptide}$ | FICI[b] |
|---|---|---|---|---|---|---|---|
| | | | antibiotic | peptide | | | |
| KL L9D | 0.5 | 18 | 0.09 | 5 | 0.18 | 0.28 | 0.46 |

| Peptide | MIC[a] of simvastatin (μM) | MIC of peptide (μM) | MIC of combination (μM) | | FICI$_{simvastatin}$ | FICI$_{Peptide}$ | FICI[b] |
|---|---|---|---|---|---|---|---|
| | | | simvastatin | peptide | | | |
| KL L9D | 750 | 18 | 83.33 | 9 | 0.11 | 0.5 | 0.61 |

[a]Minimal inhibitory concentration was determined by <20% growth percent of positive control.
[b]The FICI (Fractional inhibitory concentration index) = MICA + B/MICA + MICB + A/MICB. FICI ≤ 0.5 for synergy, 0.5 < FICI ≤ 1 for additivity to independence, 1 < FICI ≤ 2 for antagonism, 2 ≤ FIC < 4 for inhibition.

Like KL-L9P, KL-L9D also showed synergy, but for the two compounds, the synergy of the peptide containing Pro was higher than that of the peptide containing Asp. Thus, it could be seen that this synergism was observed when the overall amphipathicity of the hydrophobic peptide was broken not only by P, but also by D.

LK-L8D having a shape similar to that of the peptide LK-L7P/L8P, which has the greatest synergy and contains two Pro residues, was also prepared, and the synergy thereof was examined. This peptide also had synergy even though it was smaller than that of KL-L9P, suggesting that a peptide whose hydrophobic portion was broken by Asp is close to a membrane-activating peptide that can loosen the outer membrane of Gram-negative bacteria, like the peptide substituted with Pro. However, in peptides whose overall amphipathicity was broken by other hydrophilic residues (for example, G, S, N, Q and E), no synergy was found.

E) Observation of Change in Synergy Using Ala-Scanning of KL-L9P

The Ala-scanning method is a good way to find out which of the 14 amino acids of the peptide is the residue as an important position in exhibiting a chemical or biological effect. Thus, this method is used in studies on many peptides. When the same method is used in the present invention, it is possible to determine which of amino acids can activate the membrane and produce a great synergy with small molecules. Thus, in the present invention, for each peptide of an Ala-scanned library, an experiment was performed to examine the synergy of each peptide with colistin. In order to find out an amino acid position having the greatest effect on the synergy of a peptide, a peptide whose synergy value changed to the greatest extent relative to the synergy between KL-L9P and colistin was selected. It can be considered that the Ala substitution position of the corresponding peptide is an amino acid residue position having the greatest effect on activation of the membrane. However, the Ala-scanned peptides, except for LK-L9PK14A, did not show a great change corresponding to 2-fold or more. Since the MIC value of LK-L9PK14A was rather better than that of LK-L9P, it is believed that lysine in this portion is not important for activation of the membrane. Next, the synergy of each peptide with colistin at ½ MIC concentration was examined, and amino acid positions could be listed from an amino acid residue position, at which the synergy changed to the greatest extent relative to KL-L9P, to an amino acid residue position at which the synergy changed to the smallest extent (Table 13).

TABLE 13

Lys-Ala Scanning Peptide Library and FICI values with colistin against *Escherichia coli* (ATCC 25922)

| Peptide | Sequence | FICI [a]Against *E. coli* Colistin & 1/2 MIC peptide | Ala-site Priority |
|---|---|---|---|
| KL-L9P | KLLKLLKKPLKLLK (SEQ ID NO: 22) | 0.58 | |
| KL-L9P/K1A | ALLKLLKKPLKLLK (SEQ ID NO: 32) | 0.71 | 5 |
| KL-L9P/K4A | KLLALLKKPLKLLK (SEQ ID NO: 33) | 0.79 | 4 |
| KL-L9P/K7A | KLLKLLAKPLKLLK (SEQ ID NO: 34) | 0.86 | 3 |
| KL-L9P/K8A | KLLKLLKAPLKLLK (SEQ ID NO: 35) | 0.97 | 2 |
| KL-L9P/K11A | KLLKLLKKPLALLK (SEQ ID NO: 36) | 1.25 | 1 |
| KL-L9P/K14A | KLLKLLKKPLKLLA (SEQ ID NO: 37) | 0.66 | 6 |

[a]The FICI value is identified as inhibitory concentration, <10% of bacterial growth of the control. FICI = MIC$_{A+B}$/MIC$_A$ + MIC$_{B+A}$/MIC$_B$. Synergism is defined as FICI ≤ 1, and additivity for independence is defined as FICI = 1-4. *Escherichia coli* (ATCC 25922) was selected as representative Gram-negative bacteria.

Since the synergies of KL-L9P/K11A, KL-L9P/K8A, KL-L9P/K7A and the like, in which the substituted alanines were located inside, decreased to the greatest extent, it was believed that the amine functional group in this site would be very important for exhibiting synergy. However, the synergy of KL-L9P/K1A or KL-L9P/K14A, substituted with Ala at each ends, did not substantially decrease. In view of the fact that the two lysine residues have no great effect on the synergy, it can be expected that a peptide consisting of 12 amino acids (excluding the two lysine residues) would also have synergy similar to that of KL-L9P and colistin.

Next, in order to examine the effect of the amino acids of the hydrophobic side on activation of the membrane, a peptide library was prepared by scanning the leucine of the hydrophobic side of KL-L9P with alanine. Table 14 below summarizes the amino acid sequence of each peptide and the MIC of each peptide against *E. coli*. As expected, due to substitution with alanine, the MIC of the amphipathic peptide decreased compared to that of the KL-L9P while the interaction of the hydrophobic side of the amphipathic peptide was weakened. In particular, the MICs of KL-L6AL9P and KLA-L9P were 80 μM and >200 μM, respectively, which greatly increased. It can be seen that the Leu position having the greatest effect on the MIC of the peptide is position 6 and that position 6 plays an important role in disrupting the interaction of the hydrophobic side of the amphipathic peptide. When 3 of 7 Leu residues in KLA-L9P were replaced with Ala, an amphipathic peptide structure was not properly formed, or the hydrophobic interaction between the cell membrane of *E. coli* and the peptide was weakened due to a decrease in the hydrophobicity of the peptide, resulting in a rapid increase in the MIC.

Next, KL-L6AL9P and KLA-L9P, the MICs of which significantly decreased, were excluded, and the synergies of the peptides with colistin were measured.

TABLE 14

Amino acid sequences of peptides obtained by scanning the KL-L9P Leu position with Ala, and MIC values of the peptides against *Escherichia coli* (ATCC 25922)

| Peptide | Sequence | MIC [μM] [a]against *E. coli* |
|---|---|---|
| KL-L9P | KLLKLLKKPLKLLK (SEQ ID NO: 22) | 12 |
| KL-L2AL9P | KALKLLKKPLKLLK (SEQ ID NO: 52) | 40 |
| KL-L3AL9P | KLAKLLKKPLKLLK (SEQ ID NO: 53) | 27 |
| KL-L5AL9P | KLLKALKKPLKLLK (SEQ ID NO: 54) | 18 |
| KL-L6AL9P | KLLKLAKKPLKLLK (SEQ ID NO: 55) | 89 |
| KL-L9PL10A | KLLKLLKKPAKLLK (SEQ ID NO: 56) | 40 |
| KL-L9PL12A | KLLKLLKKPLKALK (SEQ ID NO: 57) | 40 |
| KL-L9PL13A | KLLKLLKKPLKLAK (SEQ ID NO: 58) | 40 |
| KLA-L9P | KLAKLAKKPLKLAK (SEQ ID NO: 59) | >200 |

[a]Minimum inhibitory concentration (MIC) is defined as the peptide concentration required to inhibit growth by 20%. *Escherichia coli* (ATCC 25922) was selected as representative Gram-negative bacteria.

Table 15 represents the FICI values when ¼ MIC peptides or ½ MIC peptides are mixed with colistin. When the FICI values of ¼ MIC peptides are compared with those of ½ MIC peptides, a Leu position important for the synergy of KL-L9P can be determined. If a peptide and colistin have synergy, when the peptide changes from ¼ MIC to ½ MIC, the MIC of colistin will decrease. Namely, when a peptide having synergy with colistin changes from ¼ MIC to ½ MIC, the fraction of the peptide increases from 0.25 to 0.5, but the fraction of the colistin side decreases, and thus the total FICI value should increase to a value lower than 0.25. When KL-L5AL9P, KL-L9PL10A and KL-L9PL13A changed from ¼ MIC to ½ MIC, the FICI values thereof increased by 0.37, 0.31 and 0.29, indicating that the synergies thereof with colistin decreased rapidly.

TABLE 15

Amino acid sequences of peptides obtained by scanning the KL-L9P Leu position with Ala, and Synergism with Collistin

| | | FICI [a]Against *E. coli* | |
|---|---|---|---|
| Peptide | Sequence | Colistin & 1/4 MIC peptide | Colistin & 1/2 MIC peptide |
| KL-L9P (SEQ ID NO: 22) | KLLKLLKKPLKLLK | 0.55 | 0.74 |
| KL-L2AL9P (SEQ ID NO: 52) | KALKLLKKPLKLLK | 0.61 | 0.74 |
| KL-L3AL9P (SEQ ID NO: 53) | KLAKLLKKPLKLLK | 0.55 | 0.70 |
| KL-L5AL9P (SEQ ID NO: 54) | KLLKALKKPLKLLK | 0.49 | 0.86 |
| KL-L9PL10A (SEQ ID NO: 56) | KLLKLLKKPAKLLK | 0.49 | 0.80 |
| KL-L9PL12A (SEQ ID NO: 57) | KLLKLLKKPLKALK | 0.61 | 0.74 |
| KL-L9PL13A (SEQID NO: 58) | KLLKLLKKPLKLAK | 0.51 | 0.80 |

[a]The FICI value is identified as Inhibitory concentration, <10% bacterial growth of the control, FICI = $MIC_{A+B}/MIC_A$ + $MIC_{B+A}/MIC_B$. Synergism is defined as FICI ≤ 1, Indifferent is defined as FICI = 1-4. *Escherichia coli* (ATCC 25922) was selected as representative Gram-negative bacteria.

It can be seen that the Leu position important for the synergy of KL-L9P is position 10 next to Pro and that the kinked structure of the KL-9P peptide is important for synergy. In addition, when Leu at position 5 and position 13 were substituted with Ala, the synergy decreased, suggesting that up to 4 amino acids in both directions from the kinked structure (9 amino acids including P) are important.

When the results of hydrophilicity/hydrophobicity are comprehensively examined based on how much synergism with colistin has been reduced by the membrane activating ability or how bad the MIC is, it can be seen that which amino acid position is important. The synergy decreased in the order of positions 11, 8 and 7 in the hydrophilic side and in the order of positions 6, 5 and 10 in the hydrophobic side. Taking these results together, effective amino acids can be expressed as KPLK (SEQ ID NO: 73) (four amino acids), KKPLK (SEQ ID NO:

60) (five amino acids), LKKPLK (SEQ ID NO: 74) (six amino acids), and LLKKPLK (SEQ ID NO: 75) (seven amino acids).

F) Shape of Membrane-Activating Peptides Having Synergy

Among 84 constructed peptides, only four peptides activated the membrane and showed synergy with antibiotic compounds. Thus, when the structural characteristics of the four peptides are examined, the general properties of the membrane-activating peptides can be understood. To understand the peptide structure, CD and molecular prediction programs were introduced. Regarding CD, relatively high alpha-helical contents (KL-L9P (70%), KL-L9D (50%), LK-L8D (50%) and LK-L7PL8P (60%)) were found in membrane conditions. In contrast with this, the alpha-helical contents in water conditions were very low (less than 10%). Thus, it is expected that the peptides will have high alpha-helical contents even in bacterial outer membrane conditions. However, as shown in FIG. 15, the alpha-helical shape predicted by the molecular model prediction program was not a completely cylindrical shape (FIG. 15A), but was a kinked or bent alpha-helical shape as shown in FIGS. B-1, B-2 and B-3. In view of this fact, it is believed that the peptides having a kinked structure while maintaining amphipathicity due to their high alpha-helical content will have a maximized ability to recognize hydrophilic and hydrophobic molecules present in the membrane. It is believed that this maximized ability to recognize plays a great role in loosening the membrane without degrading the membrane so that hydrophobic small molecules that could not pass through the membrane in the absence of the peptide can penetrate and enter the membrane. Even though the peptides have this kinked shape, it is not easy to define the degree of kinking. This is because, even when the peptide shape prediction program is used, various shapes can be simultaneously present in a single peptide while showing a great difference in energy.

G) Synergy of Peptide Having Kinked Shape

In order to examine whether a peptide should necessarily contain Pro for an alpha-helical structure, the present inventors prepared peptides by introducing an artificially kinked structure through disulfide bridging. Namely, as shown in Table 16 below, a kinked shape in peptides having the same amino acid sequence as that of the KL peptide was induced either by substituting i and i+4 (or i+3) positions, which are the upper and lower portions of the alpha helix, with cysteine to bind the upper and lower portions of the alpha helix, or by linking a hydrocarbon staple linker to i and i+8 positions. After the two peptides were prepared, the synergies thereof with colistin were examined (Table 17). The two peptides all had partial synergy with colistin, although the partial synergy was weaker than that of the Pro-containing peptide. In addition, a mixture of the peptide, colistin and linezolid also showed synergy (Table 18). Although the synergy was smaller than that of KL-L9P, it is encouraging that the peptides having the kinked structure caused by disulfide bridging showed clear synergy. In addition, the concentrations of colistin and linezolid were similar to or slightly higher than the MIC concentration obtained in the presence of KL-L9P and are still significant, and the MICs of the kinked peptides were significantly better than that of KL-L9P, indicating that the peptides can be used at reduced concentrations. The fact that the toxicity of the alpha-helical structure against host cells can be reduced due to the kinked structure can also be the advantage of the peptides. Even if an amphipathic peptide is not kinked by introduction of Pro, when an artificially kinked structure in the peptide is formed, the peptide can activate the membrane of Gram-negative bacteria and kill the bacteria when co-administered with various compounds.

TABLE 16

Amino acid sequences of disulfide kink peptides and MIC values against *Escherichia coli* (ATCC 25922)

| Peptide | Sequence[a] | MIC [µM] [b]Against E. coli |
|---|---|---|
| KL-L9P | KLLKLLKKPLKLLK (SEQ ID NO: 22) | 20 |
| 7, 10 kink | KLLKLL<u>C</u>KL<u>C</u>KLLK (SEQ ID NO: 38) | 1.1 |
| 8, 12 kink | KLLKLLK<u>C</u>LLK<u>C</u>LK (SEQ ID NO: 39) | 1.1 |
| st 3, 11 | KLR$_8$KLLKKPLS$_5$LLK (SEQ ID NO: 40) | 2.5 |

[a]Underlined sequences denote peptides with disulfide bridging between the terminal Cys residues.

[b]Minimum inhibitory concentration (MIC) is defined as the peptide concentration required to inhibit growth by 20%. *Escherichia coli* (ATCC 25922) was selected as representative Gram-negative bacteria.

TABLE 17

Synergies of peptides having kinked structure with colistin

*E. coli* ATCC 25922

| Peptide | MIC[a] of colistin (µM) | MIC of peptide (µM) | MIC of combination (µM) antibiotic | MIC of combination (µM) peptide | FICI$_{antibiotic}$ | FICI$_{Peptide}$ | FICI[b] |
|---|---|---|---|---|---|---|---|
| 7, 10 kink | 0.15~0.30 | 1.1 | 0.081 | 0.63 | 0.31 | 0.58 | 0.89 |
| 8, 12 kink |  | 1.1 | 0.065 | 0.59 | 0.30 | 0.56 | 0.86 |
| st 3, 11 |  | 2.5 | 0.12 | 0.61 | 0.27 | 0.59 | 0.86 |

[a]Minimal inhibitory concentration was determined by <20% growth percent of positive control.

[b]The FICI (fractional inhibitory concentration index) = MIC$_{A+B}$/MIC$_A$ + MIC$_{B+A}$/MIC$_B$. FICI < 0.5 for synergy, 0.5 ≤ FICI < 1 for partial synergy, 1 ≤ FICI ≤ 2 for additivity to independence, and FIC > 2 for antagonism.

TABLE 18

Synergy between peptide having kinked structure and colistin or linezolid
E. coli ATCC 25922

| Peptide | MIC[a] of colistin (μM) | MIC of linezolid (μM) | MIC of peptide (μM) | MIC of combination (μM) | | | FICI$_{colistin}$ | FICI$_{linezolid}$ | FICI$_{Peptide}$ | FICI[b] |
|---|---|---|---|---|---|---|---|---|---|---|
| | | | | colistin | linezolid | peptide | | | | |
| 7, 10 kink | 0.15~0.30 | 59 | 1.1 | 0.081 | 22 | 0.44 | 0.33 | 0.37 | 0.37 | 1.1 |
| 8, 12 kink | | | 1.1 | 0.065 | 22 | 0.44 | 0.29 | 0.37 | 0.42 | 1.1 |
| st 3, 11 | | | 2.5 | 0.060 | 15 | 0.30 | 0.25 | 0.33 | 0.11 | 0.70 |

Synergy effect was evaluated by the novel antibiotic interaction assay (Wimley, 2015). Broth microdilution technique (2/3 dilution) was used with MH Broth. Antibiotic, peptide treated E. coli was incubated 18 hours at 37° C. incubator.
[a]Minimal inhibitory concentration was determined by <20% growth percent of positive control.
[b]The FICI (Fractional inhibitory concentration index) = MIC$_{A+B+C}$/MIC$_A$ + MIC$_{B+A+C}$/MIC$_B$ + MIC$_{C+A+B}$/MIC$_C$. FICI < 1 for synergy, 1 ≤ FICI < 2 for partial synergy, 2 ≤ FICI ≤ 3 for additivity to independence, and FIC > 3 for antagonism.

H) Membrane-Activating Property of Buforin (Natural Peptide Kinked by Pro, which is not LK or KL Peptide)

The present inventors contemplated whether not only model peptides having 100% amphipathicity, like the LK or KL peptide, but also peptides having a suitable level of amphipathicity, or many kinds of naturally occurring antimicrobial peptides and cell-penetrating peptides, would have the properties of such Gram-negative bacteria-specific membrane-activating peptides. This is because the phenomenon discovered by the present inventors can be a very reasonable method by which curcumin, resveratrol and the like, which are active ingredients produced by plants, can kill Gram-negative bacteria that penetrated plants. Namely, curcumin has the ability to kill Gram-negative bacteria, but in the absence of this membrane-activating peptide, it can kill bacteria even when it is used at very high concentrations. However, if membrane-activating peptides such as the KL or LK peptide discovered by the present inventors are present in nature, curcumin can enter bacteria by use of these peptides and can kill the bacteria even at very low concentrations due to its synergy.

Buforin (21 amino acids; TRSSRAGLQFPVGRVHRLLRK: SEQ ID NO: 50) which is a portion of naturally occurring histone protein 2A has a wide spectrum of antibiotic effects. Many antibiotic effects result from the property of degrading the membrane, this buforin has the property of penetrating the bacterial membrane. After it penetrates the bacterial membrane and enters the bacteria, it kills the bacteria by binding to DNA or RNA in the bacteria. In order to weaken the property of penetrating the bacterial membrane while maintaining the ability to activate the membrane, the present inventors produced buforin 5-20 (amino acids 5 to 20 of buforin II; RAGLQFPVGRVHRLLRK: SEQ ID NO: 51) by reducing 21 amino acids of buforin II to 16 amino acids. This buforin was a previously examined peptide which has no hemolytic activity, has no activity against Gram-positive bacteria and has slight activity against Gram-positive bacteria. Furthermore, these three properties can be very similar to those of the model peptide LK-L9P developed by the present inventors.

Next, the buforin 5-20 peptide was synthesized, the MIC value thereof against E. coli, and whether the buforin 5-20 peptide would activate the Gram-negative bacterial membrane and have synergy with colistin or linezolid was examined. First, the MIC value of buforin 5-20 was 20 μM, which was substantially the same as previously reported. The FICI values of buforin 5-20 with colistin and linezolid were 0.5 and 0.7, respectively, as measured by the method of Winley. This suggests that buforin 5-20 has the ability to activate the Gram-negative bacterial membrane, which is lower than that of KL-L9P, and thus it has synergy with other antibiotics. Although the amino acid sequence of buforin 5-20 significantly differs from that of KL-L9P, buforin 5-20 has the following properties which are accurately consistent with the membrane-activating properties of LK-L9P and its derivatives: 1) it has an amphipathic alpha-helical shape; 2) it has an alpha-helical structure kinked (or bent) by Pro, and the kinked portion is hydrophobic; 3) it has a positively charged amino acid content of 35% (6/16); 4) it has a hydrophobic amino acid content of 35% (6/16); 5) it has no hemolytic activity against host cells and no activity against Gram-positive bacteria; and 6) it retains weak activity against Gram-negative bacteria (MIC=10-20 μM). Thus, the above-described six properties may be defined as the general properties of Gram-negative bacterial membrane-activating peptides.

Buforin 5-20 is highly hydrophilic, because the retention time thereof in HPLC is very short among the same sizes of amino acids (i.e. 16 amino acids). In addition, as described above, these results are consistent with the results obtained for KL-L9P which differs from its isomers (containing proline at other positions) in that it is highly hydrophilic so that it will have the shortest retention time in HPLC conditions. One of the general properties of membrane-activating peptides is that they contain positively charged portion (or hydrophobic portion) and are hydrophilic overall.

Example 9: General Properties of Compounds Having Synergy with Membrane-Activating Peptide Small molecules compounds having synergy with membrane-activating peptides were examined using conventional antibiotics and pharmacological compounds. The small molecules compounds examined include conventional antibiotics, including linezolid, which are used against Gram-positive bacteria; NSAID series small molecules Compounds which are frequently used for anti-inflammatory and fever remedy purposes; statin-based small molecules compounds which are hyperlipidemia therapeutic agents; and nutraceutical compounds which are well known to have medicinal effects but have not yet been approved for use as drugs.

Although the kinds of membrane-activating peptides are diverse (Example 8) so that the mechanisms according to which the peptides act against the membrane may somewhat vary, the KL-L9P peptide was used to calculate synergy. This is because the synergies of this peptide with small molecules compounds can be easily determined at micromolar concentrations. Such micromolar concentrations are similar to the effective concentrations used in experiments on many kinds of Gram-negative bacterial candidate antibiotics having synergy with the peptide, and thus errors resulting from a difference in the concentrations of candidate compounds can be minimized.

The synergies of the membrane-activating peptide KL-L9P with small molecules compounds ere determined by calculating FICI values using the method of Wimley. This method is much accurate than a conventional checker-board assay. The conventional method uses ½-dilution, whereas the new method used ⅔-dilution so that whether there would be synergy could be examined while errors resulting from dilution of compounds or peptides could be minimized.

Figure 18:
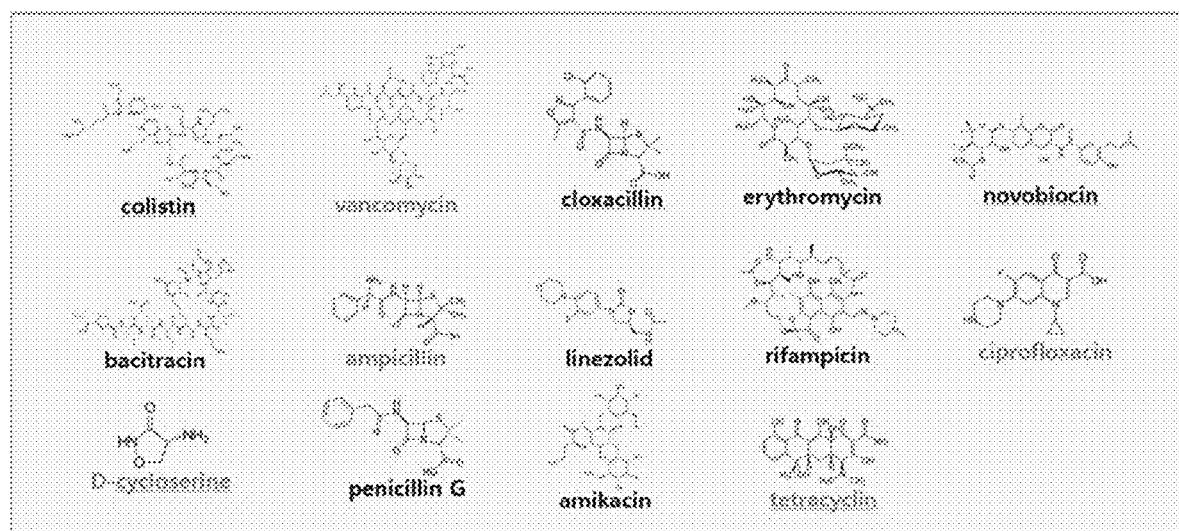
FIG. 18 assorts antibiotics, which are synergistic with KL-L9P (indicated by black), and antibiotics which are not synergistic with KL-L9P (indicated by gray).

As described already above with respect to synergy, a surprisingly high proportion (about 69%) of small molecules compounds had synergy with KL-L9P (FIG. 18).

Figure 19:
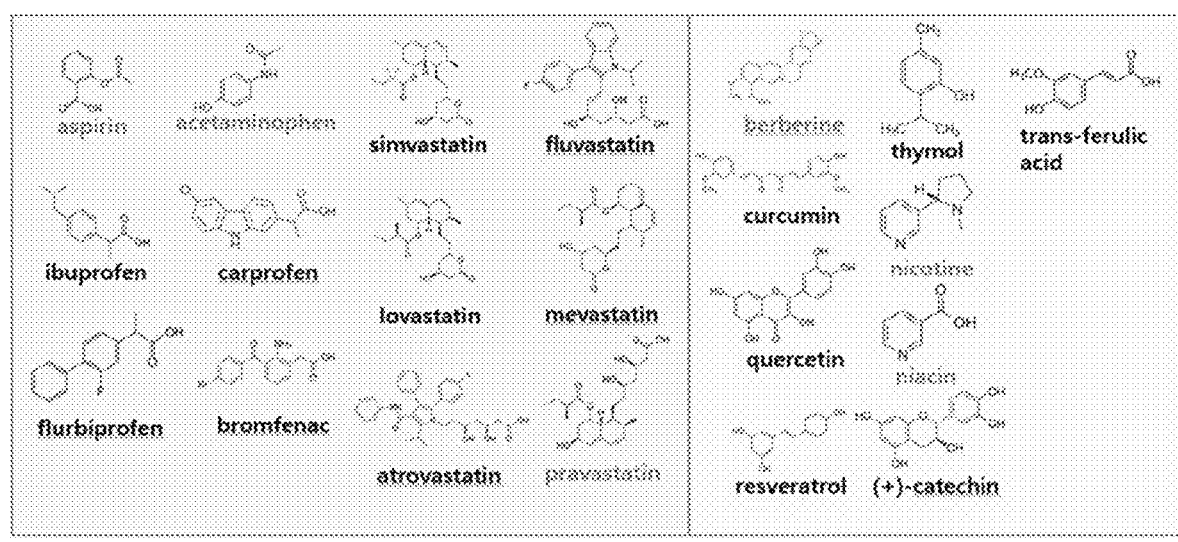
FIG. 19 assorts non-antibiotic drugs (nutraceuticals) which are synergistic with KL-L9P (black), and non-antibiotic drugs (nutraceuticals) which are not synergistic with KL-L9P (gray).

Compounds having synergy have various charges (neutrally/positively/negatively charged compounds), and thus it does not appear that recognition with the positively charged peptide is a source of synergy. This is because amphipathic peptides such as colistin show strong synergy with the KL-L9P peptide, and simple and electrically negative compounds such as ibuprofen are also strongly synergistic while having similar values. For simvastatin and lovastatin which have very similar structures, simvastatin shows very strong synergy, whereas lovastatin shows synergy which is greatly lower than that of simvastatin. It is very interesting that two enantiomers of ibuprofen all have synergy (FIG. 19).

However, not all compounds are synergistic. Among antibiotics, D-cycloserine, vancomycin, tetracyclin, ciprofloxacin and the like were not synergistic. Among these compounds, vancomycin is an inhibitor of enzymes that are not highly expressed in Gram-negative bacteria, and tetracyclin and ciprofloxacin have a mechanism that enters bacteria through the porin protein present in the bacterial membrane. Among NSAIDs, aspirin and acetaminophen were not synergistic. These substances have very low molecular weights. Among nutraceuticals, it is unusual that berberine was not synergistic. This compound is a compound originally known as an antibiotic, and thus was believed to be naturally synergistic, but was not synergistic so that the FICI value would reach 1.5.

Then, the general properties of small molecules synergistic with the membrane-activating peptide were examined. Among the antibiotics, the compounds that were not synergistic were compounds that enter bacteria through the porin protein. In addition, aspirin, acetaminophen and the like were very small molecules having a molecular weight of 200 or less. Namely, these are excessively hydrophilic, and thus are expected not to penetrate the membrane directly. In view of this fact, synergistic compounds should enter bacteria through the hydrophobic membrane made loose by the membrane-activating peptide, and if so, it appears that the compounds should be highly hydrophobic in nature. This hydrophilicity and hydrophobicity are expressed by the partition coefficient log P value. This value is the log of the ratio of the concentration of a compound dissolved in hydrophobic octanol to the concentration of the compound dissolved in the water. As log P increases, the hydrophobicity of the compound generally increases.

Whether log P which indicates the hydrophilicity/hydrophobicity of a compound has a correlation with synergy was examined. In general, as the FICI value decreases, synergy increases. Thus, a correlation between the inverse thereof and log P was plotted. As shown in the following FIG. 13, when KL-L9P was used as a membrane-activating peptide, the hydrophobicity of a compound had a strong correlation with the synergy. Namely, as the hydrophobicity of the compound increases, the synergy thereof increases. Synergy is defined as an FICI value of 1 or less, and thus when a compound has a lopP value of 0.19 or more, the compound can be synergistic. However, there are exceptions to this definition. Although colistin and linezolid are highly hydrophilic molecules, they have good synergy. In addition, although aspirin, atorvastatin and the like are highly hydrophobic in nature, they are not synergistic. The characteristic of a compound having good synergy while being hydrophilic in nature is the property of being positively charged under physiological pH conditions. A compound which is not synergistic despite its hydrophobicity is highly likely to be negatively charged under physiological pH conditions. Considering that the inner membrane or outer membrane surface of Gram-negative bacteria is negatively charged, the reason why such exceptional compounds are synergistic can be understood. Namely, a positively charged compound can bind to the membrane surface and enter the bacteria by the membrane-activating peptide, whereas a negatively charged compound has a great potential to lose opportunity due to the repulsive force with anions on the bacterial surface (FIG. 11).

Figures 11, 12:
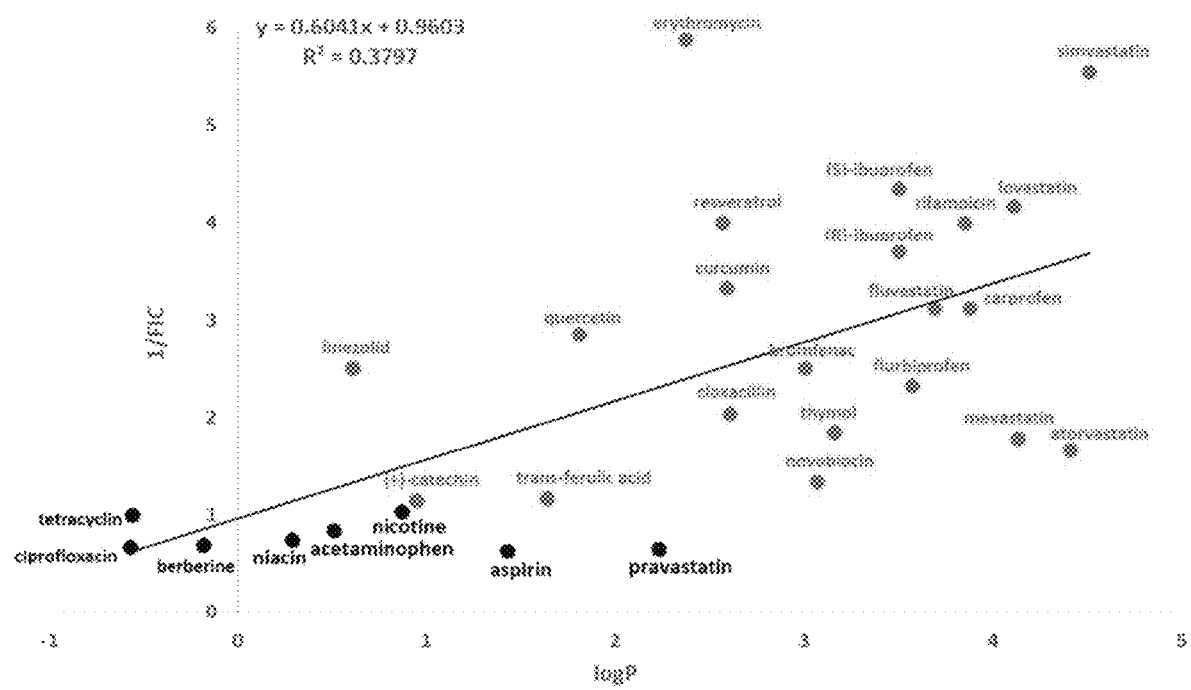
FIG. 11 schematically shows the correlation between a synergistic effect and log P which indicates the hydrophilicity or hydrophobicity of compounds that are co-administered.
FIG. 12 schematically shows the correlation between a synergistic effect and the molecular weight of compounds that are co-administered.

The correlation between molecular weight and synergy was also plotted (FIG. 12). Although there is no great correlation between molecular weight and synergy, most compounds having a molecular weight lower than 200 are not synergistic. Combined with the results of hydrophilicity/hydrophobicity as described above, it can be seen that relatively hydrophobic compounds having a molecular weight of 200 or higher can pass through the Gram-negative bacterial outer membrane by the membrane-activating peptide and bind to their target inside and outside the bacteria, thereby exhibiting antibacterial activity. The mechanisms of repositionable drugs (e.g., ibuprofen, simvastatin, etc.) having new antibiotic effects, except for antibiotics whose mechanisms were already identified, should be newly found, but are beyond the scope of the present invention and are not covered by the present invention.

Figure 13:
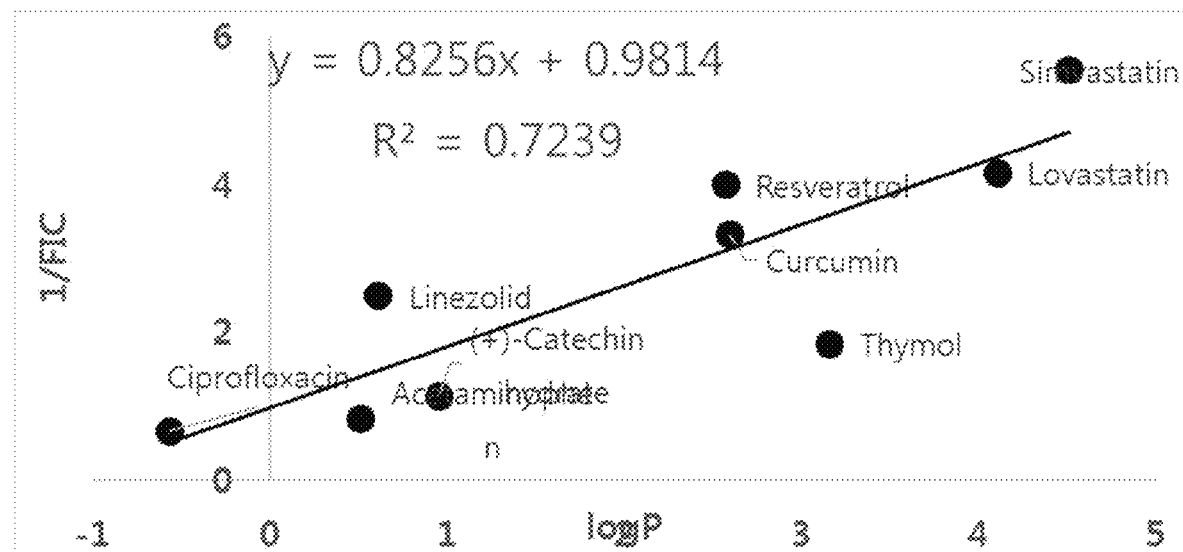
FIG. 13 schematically shows the correlation between a synergistic effect and log P of entire candidate compounds that are co-administered.

As shown in FIG. 13, there was a correlation between the log P values of compounds, which can be synergistic with the membrane-activating peptide, and the synergy with the compounds, but the correlation was not so strong. In order to further analyze this correlation and identify the general properties of synergistic compounds, synergistic compounds were divided into three groups: a non-charged compound group (charge 0), a negatively charged compound group (charge −1), and a positively charged compound group.

First, the log P value and synergy of the non-charged compounds showed a very good correlation. This indicates that the correlation is more consistent than the correlation with synergy of all compounds.

However, for the negatively charged or positively charged compounds, it appears that the hydrophilicity/hydrophobicity ratio of the compounds, which is generally calculated from log P, does not fit well. For this reason, the value obtained by dividing the polar surface area of the compound by the molecular weight was introduced as a new variable. This is an index indicating the surface area of a polar molecule per molecular weight (PSA/MW). Thus, as this value decreases, the polar surface area per molecular weight decreases, and as this value increases, the polar surface area per molecular weight relatively increases. For negatively charged compounds, this value and the synergy of the compound were inversely correlated. This suggests that as the polar surface area per molecular weight decreases, the synergy increases.

Figure 14:
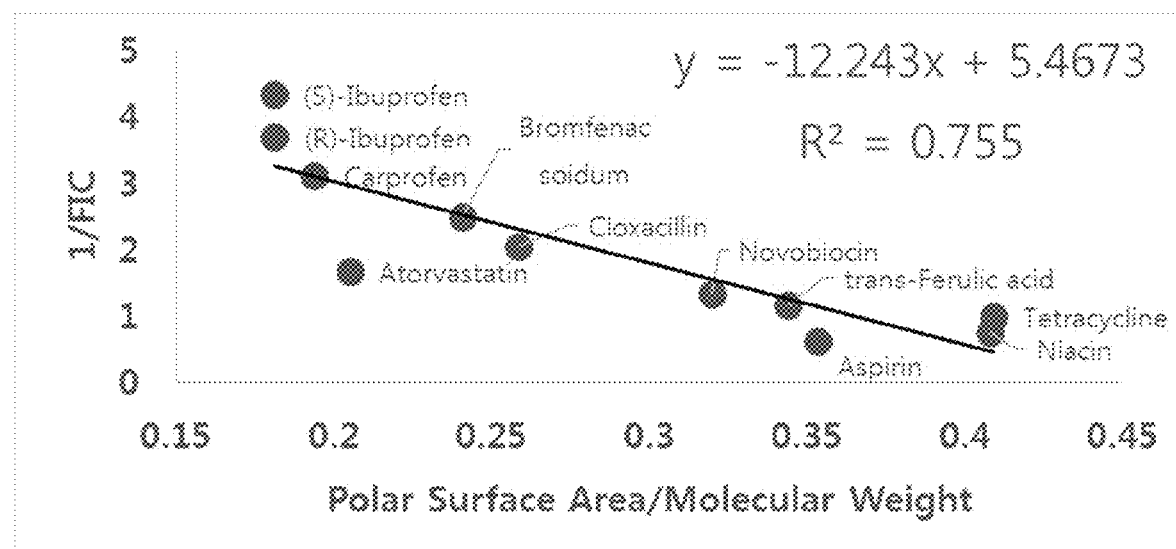
FIG. 14 schematically shows the correlation between a synergistic effect and the polar surface area and molecular weight of negatively or positively charged compounds.

For positively charged compounds, correlation was examined using the polar surface area per molecular weight (PSA/MW) as the x-axis and 1/FIC value indicating synergy as the y-axis (FIG. 14). As expected, when the polar surface area was relatively large, synergy had a great correlation therewith. This suggests that as the positively charged surface area increases, the synergy value can increase.

Taken together, synergy has a great correlation with the hydrophobicity of a compound (there is a correlation between overall log P and synergy). However, there are a few exceptions. Namely, for negatively charged compounds, the synergy increases as the charged portion becomes smaller, and for positively charged molecules, the synergy increases as the positively charged portion becomes larger. This demonstrates that, because Gram-negative bacterial portions are negatively charged, a positively charged molecule is advantageous over a negatively charged molecule in entering bacteria by the membrane-activating peptide.

As a result, it is believed that new antimicrobial activity against bacteria is created according to the mechanism by which a compound that could not pass the Gram-negative bacterial outer membrane (particularly a hydrophobic portion) enters bacteria by the membrane-activating peptide. Although substances with a relatively low molecular weight are relatively hydrophobic, they can enter bacteria with the aid of portions other than the membrane, such as porin. The fact that these molecules have relatively weak synergy with the membrane-activating peptide is another evidence that explain the above-described mechanism. Positively charged substances have better synergy than negatively charged substances. It does not seem to be irrelevant to negative charges on the bacterial surface, but it is not clear whether it is due to negative charges in the outer membrane or inner membrane.

The correlation of positively charged molecules was not shown, because the amount of data was small. The correlation of compounds that are synergistic with the membrane-activating peptide can be defined as hydrophobic (log P>0.19) compounds. However, compounds having an excessively low molecular weight (M.W.<200) have small synergy, and compounds that are problematic in terms of water solubility due to their excessively great log P also cannot show increased synergy. Thus, it is expected that actually synergistic compounds will have about 0.19<log P<5.0.

Example 10: Combined Treatment with Peptide

The present invention is directed to a method of finding out a new antibiotic against Gram-negative bacteria by use of KL-L9P that specifically activates the Gram-negative bacterial membrane, and to a combined treatment agent for suppressing Gram-negative bacteria, which comprises the peptide. Namely, the membrane-activating peptide is synergistic with 65% of many therapeutic agents for other purposes, and helps repurpose these therapeutic agents as therapeutic agents against Gram-negative bacteria. Among these therapeutic agents, compounds having the greatest synergy include NSAIDs such as (S)-ibuprofen, statins such as simvastatin, and natural substances such as curcumin. One of conventional drugs that stimulate the outer membrane of Gram-negative bacteria is colistin which is synergistic with the KL-L9P peptide. It was found that both colistin and KL-L9P touch the outer membrane, but there is a slight difference in the mechanisms of action thereof. In the presence of the two peptides having the ability to activate the outer membrane, a repositioning drug showed increased synergy (FICI value smaller than 0.3). This suggests that it has the effect of killing Gram-negative bacteria at a concentration which is at least 10-fold lower than the MIC shown when the three compounds (LK-L9P, colistin and repositioning drug) are used alone. By using it well, it is possible to kill Gram-negative bacteria even at very low concentrations avoiding the toxicity and cytotoxicity of the three compounds, suggesting that the repositioning drug can be used as a new antibiotic that may be applied to Gram-negative bacteria having resistance. Tables 19 to 23 below shows MICs against *E. coli* when each of linezolid (Table 19), cloxacillin (Table 20), curcumin (Table 21) and ibuprofen (Table 22) among repositioning drugs was mixed with KL-L9P and colistin to form combinations of two or three compounds.

In Table 19, the first line (black) shows MIC against *E. coli* when the three compounds were used alone; the second line (gray) shows MIC against *E. coli* when only two of the three compounds were used for treatment; and the third line (white) shows MIC against *E. coli* when all the three compounds were used as a mixture for treatment. In Table 20, the first line (black) shows MIC against *E. coli* when the three compounds were used alone; the second line (gray) shows MIC against *E. coli* when only two of the three compounds were used for treatment; and the third line (white) shows MIC against *E. coli* when all the three compounds were used as a mixture for treatment. In Table 21, the first line (black) shows MIC against *E. coli* when the three compounds were used alone; the second line (gray) shows MIC against *E. coli* when only two of the three compounds were used for treatment; and the third line (white) shows MIC against *E. coli* when all the three compounds were used as a mixture for treatment. In Table 22, the first line (black) shows MIC against *E. coli* when the three compounds were used alone; the second line (gray) shows MIC against *E. coli* when only two of the three compounds were used for treatment; and the third line (white) shows MIC against *E. coli* when all the three compounds were used as a mixture for treatment. In Table 23, the first line (black) shows MIC against *E. coli* when the three compounds were used alone; the second line (gray) shows MIC against *E. coli* when only two of the three compounds were used for treatment; and the third line (white) shows MIC against *E. coli* when all the three compounds were used as a mixture for treatment.

In all the cases, MIC was the highest when the three compounds were used alone. Treatment with only two of the three compounds showed a lower MIC, and treatment with a mixture of the three compounds showed the lowest MIC.

TABLE 19

Synergy between KL-L9P, colistin and linezolid
MIC (μM) against *E. coli* ATCC

| 1 compound alone | | Combinations of two compounds | | | | | | Combination of 3 compounds | |
| --- | --- | --- | --- | --- | --- | --- | --- | --- | --- |
| KL-L9P | 15 | KL-L9P | 2.4 | KL-L9P | 2.6 | | | KL-L9P | 1.1 |
| colistin | 1 | colistin | 0.17 | | | colistin | 0.60 | colistin | 0.06 |
| linezolid | 70 | | | linezolid | 16 | linezolid | 36 | linezolid | 6.7 |

TABLE 20

Synergy between KL-L9P, colistin and cloxacillin
MIC (μM) against *E. coli* ATCC

| 1 compound alone | | Combinations of two compounds | | | | | | Combination of 3 compounds | |
|---|---|---|---|---|---|---|---|---|---|
| KL-L9P | 15 | KL-L9P | 2.4 | KL-L9P | 3.0 | | | KL-L9P | 1.6 |
| colistin | 1 | colistin | 0.17 | | | colistin | 0.63 | colistin | 0.08 |
| cloxacillin | 70 | | | cloxacillin | 18 | cloxacillin | 38 | cloxacillin | 9.4 |

TABLE 21

Synergy between KL-L9P, colistin and curcumin
MIC (μM) against *E. coli* ATCC

| 1 compound alone | | Combinations of two compounds | | | | | | Combination of 3 compounds | |
|---|---|---|---|---|---|---|---|---|---|
| KL-L9P | 15 | KL-L9P | 2.4 | KL-L9P | 1.9 | | | KL-L9P | 1.1 |
| colistin | 1 | colistin | 0.17 | | | colistin | 0.30 | colistin | 0.08 |
| curcumin | 300 | | | curcumin | 79 | curcumin | 83 | curcumin | 20 |

TABLE 22

Synergy between KL-L9P, colistin and ibuprofen
MIC (μM) against *E. coli* ATCC

| 1 compound alone | | Combinations of two compounds | | | | | | Combination of 3 compounds | |
|---|---|---|---|---|---|---|---|---|---|
| KL-L9P | 15 | KL-L9P | 2.4 | KL-L9P | 2.0 | | | KL-L9P | 1.1 |
| colistin | 1 | colistin | 0.17 | | | colistin | 0.55 | colistin | 0.08 |
| (S)-ibuprofen | 12000 | | | (S)-ibuprofen | 420 | (S)-ibuprofen | 830 | (S)-ibuprofen | 98 |

TABLE 23

Synergy between KL-L9P, colistin and simvastatin
MIC (μM) against *E. coli* ATCC

| 1 compound alone | | Combinations of two compounds | | | | | | Combination of 3 compounds | |
|---|---|---|---|---|---|---|---|---|---|
| KL-L9P | 15 | KL-L9P | 2.4 | KL-L9P | 1.3 | | | KL-L9P | 0.79 |
| colistin | 1 | colistin | 0.17 | | | colistin | 0.25 | colistin | 0.06 |
| simvastatin | >500 | | | simvastatin | 53 | simvastatin | 71 | simvastatin | 33 |

There is no drug for eradicating Gram-negative bacteria having resistance, and thus new types of drugs should be discovered as soon as possible in an unusual way. One unusual method is to loosen the outer membrane of Gram-negative bacteria so that a compound can pass through the outer membrane. A library of proline-containing amphipathic peptides was constructed, and KL-L9P having the ability to activate the Gram-negative bacterial membrane was selected as a candidate. It was found that this peptide does not touch host cells, and thus is not toxic to the host cells, while it has the property of penetrating the outer membrane of Gram-negative bacteria. However, it has no ability to degrade the membrane, and thus has the effect of loosening the membrane while staying in the membrane for a long time. Due to this effect, the peptide helps other candidate antibiotics pass through the membrane. Among compounds whose antimicrobial activities were tested, many compounds whose antimicrobial effects against Gram-negative bacteria were not known could have antimicrobial effects in the presence of the bacterial membrane-activating peptide. For example, linezolid could kill Gram-negative bacteria at 16 μM. It could be seen that when another compound colistin that loosens the bacterial outer membrane, together with the KL-L9P peptide, stimulated the membrane of Gram-negative bacteria, the synergy of synergistic compounds further increased. In this case, linezolid easily killed *E. coli* at a concentration of only 6.7 μM. It was demonstrated that when the amphipathic alpha-helical shape of this membrane-activating peptide was a bent shape, the peptide had maximized effects and also had no toxicity to host cells. It was found that the compounds that are synergistic with the membrane-activating peptide showed effects when they were hydrophobic molecules (log P>0.19) having a molecular weight of 200 or higher. Thus, many kinds of substances capable of killing Gram-negative bacteria can be derived. This fact suggests that the reason why it has been difficult to develop Gram-negative bacteria-specific antimicrobial agents is because of the outer membrane of Gram-negative bacteria. In addition, the present invention demonstrates that the presence of a membrane-activating peptide that can loosen the outer membrane to allow small molecules having no membrane-penetrating ability to enter bacteria is the fastest and reliable method for developing Gram-negative bacteria-specific antimicrobial agents.

INDUSTRIAL APPLICABILITY

As descried above, according to the present invention, the development of a Gram-negative bacterial membrane-specific activating peptide makes it possible to replace conventional antibiotics (e.g., colistin) having serious side effects such as nephrotoxicity and neurotoxicity. In addition, when the peptide is co-administered with colistin, a great synergistic effect can be obtained. Thus, strongly toxic colistin may be administered at a concentration which is at least 10-fold lower than conventional concentrations, thereby killing Gram-negative bacteria while minimizing side effects. If the outer membrane-loosening effect of the membrane-activating peptide according to the present invention can be combined with the outer membrane-loosening effect of colistin, it is possible to kill Gram-negative bacteria using the peptide and colistin in combination with an antibiotic discovered by the present inventors, while the developed membrane-activating peptide and colistin are used at reduced concentrations. When the membrane-activating peptide is used alone or in combination with colistin to loosen the outer membrane of Gram-negative bacteria, many kinds of compounds which have been difficult to penetrate bacteria due to the non-loose membrane can penetrate bacteria. In addition, it is possible to accurately screen whether a candidate compound penetrates the outer membrane of Gram-negative bacteria by the peptide of the present invention and functions as an antibiotic, and thus the possibility of discovering a novel antibiotic is also high.

It will be apparent to those skilled in the art to which the present invention pertains that various applications and modifications can be made based on the above description without departing from the scope of the present invention.

The invention claimed is:

1. A method for killing Gram-negative bacteria, comprising administering i) a Gram-negative bacterial membrane-penetrating peptide comprising the sequence of SEQ ID NO: 14, 19, 22 or 30 and ii) an antibiotic, wherein the antibiotic has an antimicrobial activity for Gram-positive bacteria.

2. The method of claim 1, wherein the antibiotic having an antimicrobial activity for Gram-positive bacteria is cloxacillin or linezolid.

3. A method for killing Gram-negative bacteria, comprising administering i) a Gram-negative bacterial membrane-penetrating peptide comprising the sequence of SEQ ID NO: 14, 19, 22 or 30 and ii) a drug, wherein the drug is resveratrol, curcumin, ibuprofen, quercetin, simvastatin, lovastatin or atorvastatin.

* * * * *

UNITED STATES PATENT AND TRADEMARK OFFICE
CERTIFICATE OF CORRECTION

Page 1 of 1

PATENT NO. : 11,123,400 B2
APPLICATION NO. : 15/761089
DATED : September 21, 2021
INVENTOR(S) : Yu It is certified that error appears in the above-identified patent and that said Letters Patent is hereby corrected as shown below:

In the Specification

Column 2, Line 25, "(AMPS)" should read -- (AMPs) --.

Column 2, Line 29, "AMPS" should read -- AMPs --.

Column 4, Line 53, "(AMPS)" should read -- (AMPs) --.

Column 4, Line 60, "AMPS" should read -- AMPs --.

Column 12, Line 55, "(AMPS)" should read -- (AMPs) --.

Column 12, Line 64, "AMPS" should read -- AMPs --.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*